(12) United States Patent
Shinya et al.

(10) Patent No.: US 7,358,233 B2
(45) Date of Patent: Apr. 15, 2008

(54) TETRONIC ACID DERIVATIVE

(75) Inventors: Kazuo Shinya, Tokyo (JP); Takashi Tsuruo, Tokyo (JP); Akihiro Tomida, Tokyo (JP); Hae-Ryong Park, Tokyo (JP)

(73) Assignee: Toudai TLO, Ltd, Tokyo (JP)

( * ) Notice: Subject to any disclaimer, the term of this patent is extended or adjusted under 35 U.S.C. 154(b) by 378 days.

(21) Appl. No.: 10/852,766

(22) Filed: May 21, 2004

(65) Prior Publication Data

US 2005/0014232 A1   Jan. 20, 2005

Related U.S. Application Data

(63) Continuation-in-part of application No. PCT/JP02/09279, filed on Sep. 11, 2002.

(30) Foreign Application Priority Data

Nov. 22, 2001   (JP) ............................. 2001-357114

(51) Int. Cl.
*A61K 31/70* (2006.01)
*C07H 17/08* (2006.01)
*C12P 17/00* (2006.01)

(52) U.S. Cl. ........................ 514/28; 536/7.1; 435/117

(58) Field of Classification Search .................. 514/28; 536/7.1; 435/117
See application file for complete search history.

(56) References Cited

FOREIGN PATENT DOCUMENTS

| EP | 0 033 840 A2 | 8/1981 |
|---|---|---|
| JP | 6-199882 | 7/1994 |
| WO | WO 99/22220 A1 | 5/1999 |
| WO | WO 99/63057 A1 | 12/1999 |
| WO | WO 02/12945 A2 | 2/2002 |

OTHER PUBLICATIONS

Park et al., "Regulation of GRP78 Transcription by Substances of Microbial Origin," (Abstract), *Society for Neuroscience's 31st Annual Meeting*, 5 pp. (Sep. 12, 2001).
Shin-ya et al., Science for Neuroscience Abstracts, 27(1):1486 (2001).
Park et al., "Versipelostatin, a novel GRP78/Bip molecular chaperone down-regulator of microbial origin," *Tetrahedron Letters*, 43:6941-6945 (2002).
Shin-ya et al., *Japan Society for Bioscience, Biotechnology, and Agrochemistry (JSBA)*, Taikai Koen Yoshishu, pp. 1(2-2Aa04),(2002).
Mallams et al., "Kijanimicin. 2. Structure and Absolute Stereochemistry of Kijanimicin," *J. Am. Chem. Soc.*, 103:3940-3943 (1981).
Jamora et al., "Inhibition of tumor progression by suppression of stress protein GRP78/BiP induction in fibrosarcoma B/C10ME," *Proc. Natl. Acad. Sci. USA*, 93(15):7690-7694 (1996).
Tsuge et al., "Novel Antibiotics Pyrisulfoxin A and B Produced by *Streptomyces californicus*," *J. Antibiot.*, 52(5):505-507 (May 1999).
Ohtsuka et al., "Tetronothiodin, A Novel Cholecystokinin Type-B Receptor Antagonist Produced by *Streptomyces* sp. NR0489," *J. Antibiot.*, 46(1):18-24 (Jan. 1993).
Yang et al., "Down-Regulation of the Endoplasmic Reticulum Chaperone GRP78/BiP by Vomitoxin (Deoxynivalenol)," *Toxicology and Applied Pharmacology*, 162(3):207-217 (2000).
Yun et al., "Glucose-regulated Stresses Confer Resistance to VP-16 in Human Cancer Cells through a Decreased Expression of DNA Topoisomerase II," *Oncology Research*, 7(12):583-590 (1995).
Tomida et al., "Drug resistance mediated by cellular stress response to the microenvironment of solid tumors," *Anti-Cancer Drug Design*, 14(2):169-177 (1999).

(Continued)

*Primary Examiner*—Leon B. Lankford, Jr.
*Assistant Examiner*—Susan Hanley
(74) *Attorney, Agent, or Firm*—Klarquist Sparkman, LLP

(57) ABSTRACT

The present inventors intended to search for substances that can regulate the expression of a molecular chaperone, GRP78, using the expression of GRP78 as an indicator. As a result, a novel tetronic acid derivative, versipelostatin compound (also known as JL68) shown in formula (I) having the activity of suppressing GRP78 expression was isolated from the metabolite of *Streptomyces versipellis* strain 4083-SVS6. Versipelostatin can be obtained from the culture supernatant by culturing the above-mentioned *Streptomyces versipellis* strain 4083-SVS6

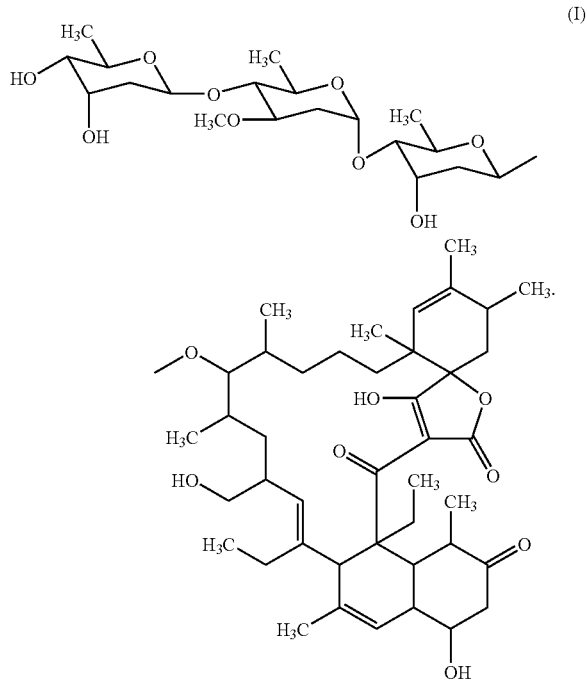

(I)

6 Claims, 16 Drawing Sheets

OTHER PUBLICATIONS

Miyake et al., "Stress Protein GRP78 Prevents Apoptosis Induced by Calcium Ionophore, Ionomycin, But Not by Glycosylation Inhibitor, Tunicamycin, in Human Prostate Cancer Cells," *Journal of Cellular Biochemistry*, 77(3):396-408 (2000).

Ogiso et al., "Proteasome Inhibition Circumvents Solid Tumor Resistance to Topoisomerase II-directed Drugs," *Cancer Research*, 60(9):2429-2434 (2000).

Lee, "The glucose-regulated proteins: stress induction and clinical applications," *TRENDS in Biochemical Sciences*, 26(8):504-510 (Aug. 2001).

Elster R, "Analysis of four *embryo-specific* mutants in *Zeas mays* revelas that incomplete radial organization of the proembryo interferes with subsequent development," *Dev Genes Evol* 2000 210:300-310.

Supplementary European Search Report from corresponding European Application No. 02 80 3567, dated Nov. 24, 2006.

TETRONIC ACID DERIVATIVE

CROSS-REFERENCE TO RELATED APPLICATIONS

This application is a continuation-in-part of PCT/JP02/09279, filed Sep. 11, 2002, which claims priority from Japanese Patent Application No. 2001-357114, filed Nov. 22, 2001, and has been published in a non-English language. This application is also a continuation-in-part of International Patent Application No. PCT/JP02/12237, filed Nov. 22, 2002. Each of these prior applications is incorporated herein by reference in its entirety.

FIELD OF THE INVENTION

The present invention relates to a novel tetronic acid derivative. More specifically, the present invention relates to an actinomycetes-derived tetronic acid derivative.

BACKGROUND OF THE INVENTION

Endoplasmic reticulum (ER) is an organelle where protein synthesis takes place and that performs folding and carbohydrate modification of produced proteins as well as protein transport. Recently, stress on the endoplasmic reticulum is focused in relation, for example, with the onset of Alzheimer's disease (AD). Endoplasmic reticulum stress is considered to be induced by the inhibition of protein folding, carbohydrate modification, protein transport, and so on, that normally occur in the endoplasmic reticulum due to physiological imbalance, external factors, etc. For example, drugs such as tunicamycin and brefeldin A induce endoplasmic reticulum stress. Tunicamycin inhibits glycosylation of proteins in the endoplasmic reticulum, causing unfolded proteins to accumulate in the endoplasmic reticulum. Such accumulation of unfolded proteins causes induction of endoplasmic reticulum stress. Brefeldin A induces endoplasmic reticulum stress by causing accumulation of proteins through the inhibition of protein transport between the endoplasmic reticulum and Golgi apparatus.

The endoplasmic reticulum has stress response mechanisms against such endoplasmic reticulum stress. For example, a stress sensor, Ire, is known to recognize unfolded proteins and promotes protein folding by inducing the expression of molecular chaperones such as GRP78. However, when endoplasmic reticulum stress cannot be overcome by such stress response mechanisms, cells are indicated to die through apoptosis.

Clinical findings on endoplasmic reticulum stress have been reported as well. Analysis of genetic predisposition to familial Alzheimer's disease revealed mutation of preselenin-1 (PS1), a membrane protein that mainly exists on the endoplasmic reticulum. In addition to the promotion of beta-amyloid production that causes senile plaque formation and such, a characteristics of Alzheimer's disease, easy induction of apoptosis due to the increased sensitivity towards various apoptosis stimuli has been reported in cells expressing this mutant PS1 (Guo, Q. et al., J. Neurosci. 17:4212-4222 (1997); Guo, Q. et al., Nat. Med. 5:101-106 (1999)). Such cell death due to PS1 mutation has been shown to be suppressed via treatments that may reduce endoplasmic reticulum stress, for example, treatment with pharmaceutical agents and antioxidants that inhibit calcium release from endoplasmic reticulum.

On the other hand, DNA topoisomerase II is known to be degraded when stress is applied to human cancer cells. Under this situation, the cancer cells are known to show resistance to the anticancer agent VP-16 whose target is DNA topoisomerase II. At the same time, the expression of GRP78, a molecular chaperone, was also found to be increased (Yun, J. et al., Oncol. Res., 7:583-590, 1995). Furthermore, examination of the use of proteasome inhibitors on the stress response and drug resistance of cancer cells in human solid cancer revealed improved sensitivity toward anticancer agents due to suppressed stress response-induced degradation of topoisomerase II (Ogiso, Y. et al., Cancer Res., 60:2429-2434, 2000).

The response to endoplasmic reticulum stress is increased in solid cancer. This increased stress response is suggested to cause resistance against antitumor agents. The sensitivity toward anticancer agents of cancer cells is reported to increase upon inhibition of the induction of the above-mentioned molecular chaperones, such as GRP78 (Koomagi, R. et al., Anticancer Res. 19:4333-6 (1999); Fernandez, P. M. et al., Breast Cancer Res. Treat. 59:15-26 (2000); Katschinski, D. M. et al., J. Cancer Res. Clin. Oncol. 127:425-32 (2001)). Furthermore, GRP78 has been found to be an excellent target of anticancer agents (Jamora, C. et al., Proc. Natl. Acad. Sci. USA 93:7690-7694 (1996); Tomida, A. and Tsuruo, T., Anti-Cancer Drug Design, 14:169-177 (1999); Miyake, H. et al., Cancer Cells. J. Cell. Biochem., 77:396-408 (2000); Lee, A. S., Trends in Biochem. Sci., 26:504-510 (2001)).

Accordingly, the regulation of the mechanism of endoplasmic reticulum stress response by the expression of molecular chaperones such as GRP78 is important for the treatment of disorders like Alzheimer's disease, and to increase the sensitivity towards anticancer agents. Furthermore, substances that may regulate such endoplasmic reticulum stress response mechanism are useful for the development of therapeutic agents for disorders, such as Alzheimer's disease, and carcinostatics.

SUMMARY OF THE INVENTION

Thus, the objective of the present invention is to provide substances that can regulate the mechanism of endoplasmic reticulum stress response and method for producing such substances.

In light of these objectives, the present inventors searched for substances that can regulate the expression of GRP78 among natural materials using the expression of one of the molecular chaperone GRP78, as an indicator. In this search, an expression vector carrying a cassette wherein a luciferase gene (as a reporter gene) is linked downstream of a GRP78 promoter, was transfected into cells and these cells were used for the screening of the substances. In the screening, the cells were contacted with various herbal medicines and metabolites of fungus, actinomycetes and such, and then tunicamycin was administered to induce endoplasmic reticulum stress. Generally, increased GRP78 expression caused by the induction of endoplasmic reticulum stress due to tunicamycin administration was observed. However, this increase in expression was suppressed in the group wherein metabolite derived from a certain actinomycetes *Streptomyces* strain was added. The inventors successfully isolated and identified a novel tetronic acid derivative, versipelostatin (also known as JL68), by purifying the active substance from the metabolite, using its activity to suppress GRP78 expression as an indicator. This activity of versipelostatin is exerted even under induced endoplasmic reticulum stress. Furthermore, the strain producing this active substance was successfully identified.

According to these findings, the present invention provides this novel tetronic acid derivative, versipelostatin, method for producing the same and microorganisms that produce the same. Specifically, the present invention relates to:

(1) a versipelostatin compound represented by following formula (I):

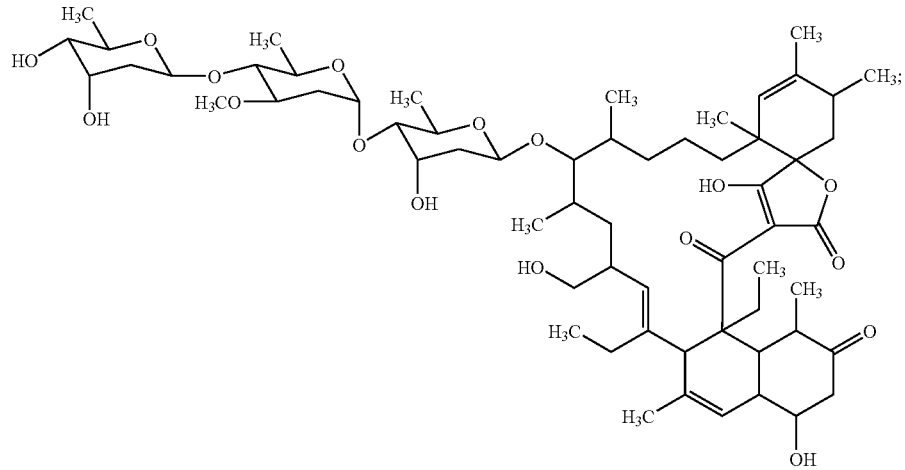

(2) a method for producing the compound of (1), which comprises the steps of culturing a strain belonging to the genus *Streptomyces* that produces the compound of (1), and collecting the compound from culture;

(3) the method of (2), wherein the strain that produces the compound of (1) is *Streptomyces versipellis* strain 4083-SVS6 (FERM BP-8179);

(4) a microorganism belonging to the genus *Streptomyces* that produces the compound of (1);

(5) the microorganism of (4), which is *Streptomyces versipellis* strain 4083-SVS6 (FERM BP-8179);

(6) a composition comprising the compound of (1) or a pharmaceutically acceptable salt thereof;

(7) an anticancer agent comprising the compound of (1) or a pharmaceutically acceptable salt thereof;

(8) the anticancer agent of (7), which induces cell death in cancer cells that are under physiological stress condition;

(9) the anticancer agent of (8), wherein the physiological stress condition is undernutritive condition or hypoxic condition; and

(10) the anticancer agent of any one of (7) to (9), which exhibits anticancer effect against solid cancer.

BRIEF DESCRIPTION OF THE DRAWINGS

In FIG. 4, wave numbers 1 through 17 represent the signals at 3454 $cm^{-1}$, 2934 $cm^{-1}$, 2360 $cm^{-1}$, 1758 $cm^{-1}$, 1711 $cm^{-1}$, 1623 $cm^{-1}$, 1575 $cm^{-1}$, 1457 $cm^{-1}$, 1381 $cm^{-1}$, 1308 $cm^{-1}$, 1208 $cm^{-1}$, 1062 $cm^{-1}$, 989 $cm^{-1}$, 934 $cm^{-1}$, 867 $cm^{-1}$, 830 $cm^{-1}$ and 730 $cm^{-1}$, respectively.

FIG. 9A shows the result of examining the dose dependence, FIG. 9B the time course, and FIG. 9C each of the stress conditions.

FIG. 10A shows the result of HT-29 cells, and FIG. 10B that of HT1080 cells.

DETAILED DESCRIPTION OF THE INVENTION

Figure 1:
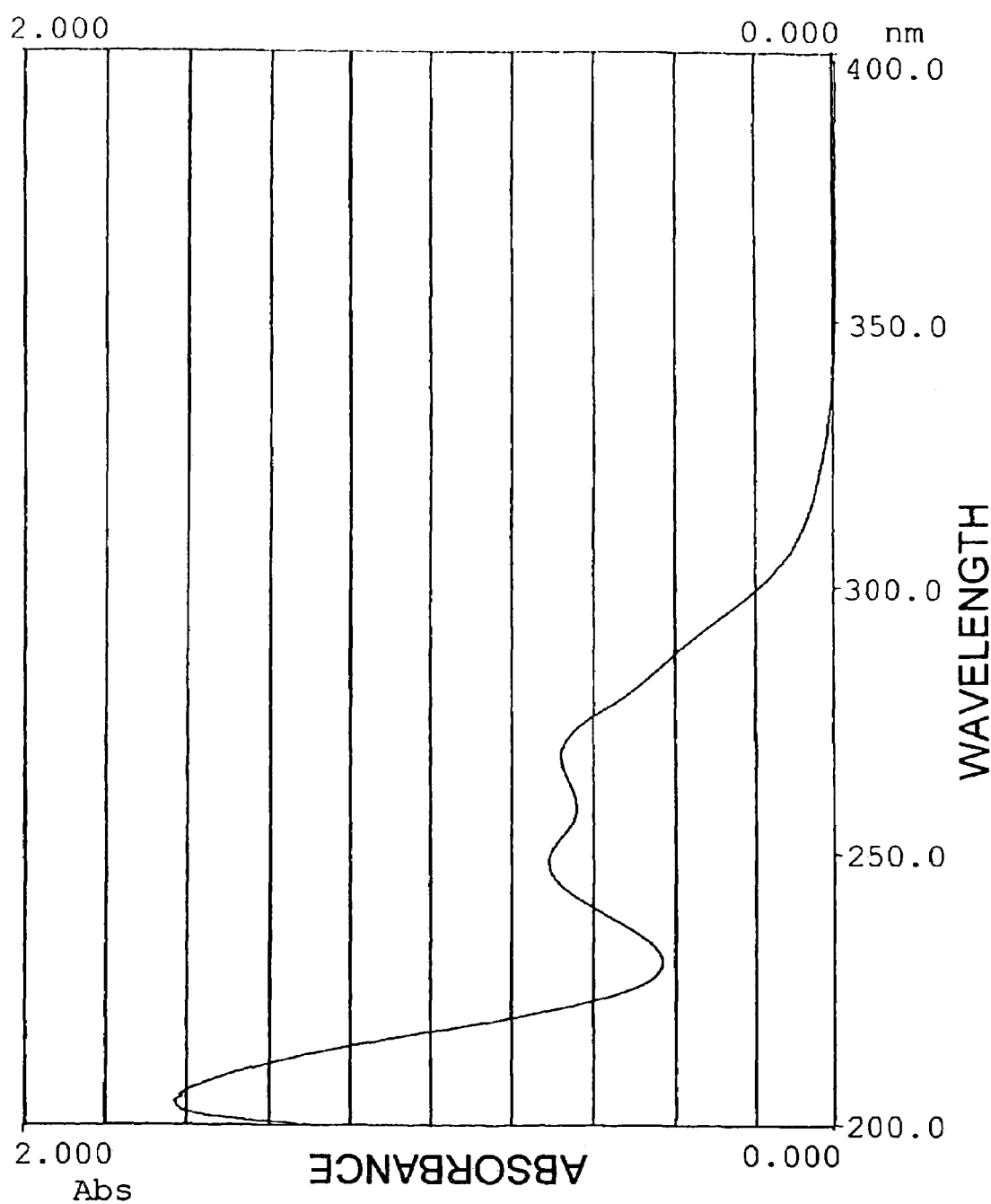
FIG. 1 shows the ultraviolet absorption spectrum of VST measured in methanol.

The novel tetronic acid derivative versipelostatin (hereinafter, abbreviated as "VST") of this invention has the structure shown above in formula (I) and physicochemical characteristics described later in the Examples. Furthermore, salts and solvates of VST are encompassed by the VST compound of this invention. Salts of VST include alkali metal salts (sodium salts, potassium salts, lithium salts, etc.), alkaline earth metal salts (calcium salts, magnesium salts, etc.), metal salts (aluminum salts, iron salts, zinc salts, copper salts, nickel salts, etc.), inorganic salts (acetates, and ammonium salts), organic amine salts (dibenzylamine salts, glucosamine salts, ethylenediamine salts, diethylamine salts, triethylamine salts, dicyclohexylamine salts, diethanolamine salts, tetramethylammonium salts, etc.), and amino acid salts (glycinates, lysinates, arginates, ornithine salts, asparaginates, etc.). Moreover, as shown in formula (I) above, VST carries hydroxyl groups in the molecule. Thus, the compound can be converted to various derivatives including ethers and esters at these functional groups. Such derivatives are included in the present invention as long as they maintain the biological activity of VST.

The above-described VST can be obtained by culturing microorganisms producing it and collecting the compound from the culture. Preferred VST-producing microorganisms that can be used include actinomycete *Streptomyces versipellis* strain 4083-SVS6. *Streptomyces versipellis* strain 4083-SVS6 was isolated from a soil sample collected in Miyoshi, Hiroshima, Japan by the present inventors. This strain was identified according to the method of International *Streptomyces* Project (ISP) and has morphological characteristics as follows.

The substrate mycelium of this actinomycetous strain does not divide. The aerial hyphae of the strain form a long major axis, and at the irregularly branched tops, spiral spore chains comprising 10 to 50 or more spores are formed. The spore has a width of 0.3 to 0.5 μm and a length of 0.7 to 1.0 μm. The spore is nonmotile, terete or oval, and has a smooth surface. When grown on glycerol-asparagine agar medium, inorganic salt starch agar medium, yeast malt agar medium, oatmeal agar medium, and the like, the spore surface turns moist black. Sclerotium, sporangium, and other special organs are not observed. The strain has a type (I) cell wall chemotype comprising LL-diaminopimelic acid, and the GC content of the DNA was 71.3 mol %.

The properties of culture upon cultivation of this actinomycetous strain on various culture media at 28° C. for 14 days are shown in Table 1. The mycelium of the colony surface had the color of a series of gray. However, after 2 weeks, the spore surface was observed to turn moist black (hygroscopic mass was observed on the spore surface). The reverse color had dim colors such as pale yellow to dark brownish gray, and did not change with pH. No diffusible pigment could be confirmed except melanin-like pigment production. The names of colors are adopted from and based on "The Color Harmony Manual" (1958) of Container Corporation of America.

TABLE 1

| Medium | Mycelium color of colony surface | Reverse color of the colony | Diffusible pigment |
|---|---|---|---|
| Sucrose nitrate agar | No aerial hypha | Pale yellow | None |
| Glucose asparagine agar | Series of gray | Pale brownish gray | None |
| Glycerol asparagine agar | Series of gray | Pale yellowish brown | None |
| Inorganic salt starch agar | Series of gray | Pale brownish gray | None |
| Tyrosine agar | No aerial hypha | Dark brownish gray | Bright brownish gray |
| Nutrient agar | No aerial hypha | Bright brownish gray | None |
| Yeast malt agar | Series of gray | Bright brown to brown | None |
| Oatmeal agar | Series of gray | Brownish gray to dark brownish brown | None |

The physiological characteristics of the actinomycetous strain when cultured at 28° C. for 2 to 21 days are shown in Table 2.

TABLE 2

| Range of growth temperature | 25-40° C. |
|---|---|
| Optimum temperature | 27-37° C. |
| Melanin-like pigment | |
| Tyrosine agar | + |
| Peptone yeast iron agar | + |
| Tryptone yeast broth | + |
| Starch hydrolysis | + |
| Gelatin liquefaction | + |
| Skim milk peptonization | + |
| Skim milk clotting | + |
| Nitrate reduction | − |
| Carbon source assimilation | |
| D-Glucose | + |
| L-Arabinose | + |
| D-Xylose | + |
| D-Fructose | + |
| Sucrose | + |
| L-Rhamnose | + |
| Raffinose | + |
| i-Inositol | + |
| D-Mannitol | + |
| Galactose | + |
| Adonitol | − |
| Cellbiose | + |
| Inulin | − |
| Melbiose | + |

In Table 2, "+" means requisite and "−" means non-requisite.

The present bacterial strain is a mesophile and produces melanin-like pigment. Since the present actinomycetous strain has a morphology wherein the spores form a spiral continuous chain, and a type (I) cell wall chemotype, it belongs to the genus *Streptomyces*. Based on the above-mentioned characteristics, strains of genus *Streptomyces* listed in "Approved List of Bacterial Names, 1980" and valid name lists thereafter were searched, and *Streptomyces versipellis* was selected as a related strain. A comparison between the present actinomycetous strain and this related strain is shown in Table 3.

TABLE 3

|  | | Present bacterial strain, VST | *Streptomyces versipellis* |
|---|---|---|---|
| Spore chain morphology | Spiral | + | + |
| Spore surface | Smooth | + | + |
| Mycelium color | Gray | + | + |
| Reverse color | Dim colors | + | + |
| pH Sensitivity | | − | − |
| Diffusible pigment production | | − | − |
| pH Sensitivity | | − | − |
| Melanin pigment production | | + | + |
| Starch hydrolysis | | + | + |
| Nitrate reduction | | − | − |
| Growth temperature | 45° C. | − | − |
| Carbon source assimilation | | | |
| Arabinose | | + | + |
| Xylose | | + | + |
| Inositol | | + | + |
| Mannitol | | + | + |
| Rhamnose | | + | + |
| Raffinose | | + | + |
| Sucrose | | + | + |
| Fructose | | + | + |

As shown in Table 3, the present actinomycetous strain closely matches the characteristics of *Streptomyces versipellis*. Since the present actinomycetous strain was most similar to *Streptomyces versipellis*, it was identified as a strain belonging to *Streptomyces versipellis*, and internationally deposited as *Streptomyces versipellis* strain 4083-SVS6 as described below.

(a) Name and address of international depository authority
 Name: National Institute of Advanced Industrial Science and Technology, International Patent Organism Depositary (Former name: National Institute of Bioscience and Human-Technology, Agency of Industrial Science and Technology, Ministry of International Trade and Industry)
 Address: AIST Tsukuba Central 6, 1-1-1 Higashi, Tsukuba, Ibaraki, Japan (Zip code 305-8566)

(b) Date of deposition (Date of original deposition): Nov. 16, 2001

(c) Accession number: FERM BP-8179

*Streptomyces versipellis* strain 4083-SVS6 was described above as the VST-producing microorganism; however, the VST-producing microorganism of the present invention is not limited thereto. The above-described characteristics of the mycelial cake are generally easily altered and are not conserved. The characteristics are well known to change naturally or to be artificially altered by physical mutagenesis means such as X-ray irradiation, chemical mutagenesis means such as ethylmethanesulfonate, or cellular engineering mutagenesis means such as gene manipulation. Therefore, the VST-producing microorganism of this invention includes natural mutant strains and artificial mutant strains of the above-mentioned actinomycetous strain belonging to VST-producing genus *Streptomyces* so long as it produces VST.

Conventional methods for culturing actinomycetes (Shinya, K. et al., J. Antibiot. 48:574-578 (1995)) may be used to culture the VST-producing actinomycetes. Specifically, a nutrient medium that appropriately contains carbon sources and nitrogen sources that may be assimilated by the microorganism, and as needed, inorganic salts, organic nutritional sources, and such, can be used as the culture medium. Examples of the above-mentioned carbon source include glucose, arabinose, xylose, fructose, sucrose, rhamnose, raffinose, inositol, mannitol, galactose, cellbiose, melbiose, molasses, starch, dextrin, cellulose, glycerol and organic acids.

Furthermore, examples of the nitrogen source include organic nitrogen sources such as peptone, meat extract, yeast extract, dry yeast, skim milk, soybean powder, corn steep liquor, cottonseed powder, casein hydrolysate, soybean protein hydrolysate, amino acids and urea; and inorganic nitrogen compounds such as nitrates and ammonium salts.

The above-mentioned carbon sources and nitrogen sources can be added to the medium alone or in combination. As necessary, inorganic salts such as sodium salts, potassium salts, ammonium salts, calcium salts, phosphates, sulfates and carbonates; trace amounts of metals such as cobalt, manganese, iron and magnesium; micronutrient, growth promoting substances, precursors and such that promote the growth of VST-producing strains or VST production may be appropriately added to the medium. Furthermore, pH of the medium is preferably set near neutral, specifically, to pH 7.0-7.6. For a liquid medium, antifoaming agents such as vegetable oil and surfactants may be appropriately added in order to suppress foaming while culturing.

Similar to conventional culture methods for actinomyces, it is preferred to perform the culture of VST-producing actinomycetes by aerobic culturing methods, such as shaking culture or culturing with aeration and stirring. The culture temperature is set at 24-30° C., preferably 27° C. Furthermore, large-scale liquid culture can be efficiently performed by, first, activating the growth of stored mycelial cake through a preculture using a small amount of medium, and then inoculating a large volume of medium with this preculture solution to perform the main culture. The culture time may be generally set 2-3 days for the preculture, and 4-6 days for the main culture. These culture conditions, such as culture temperature, aeration volume and culture time, may be appropriately adjusted and selected according to the amount of VST production. Furthermore, depending on the type of VST-producing actinomycetes and culture environment, the above-mentioned culture conditions may be altered.

To obtain VST from the culture solution, the culture solution is centrifuged or filtered to isolate the components of the mycelial cake, and the supernatant or filtrate is collected. Purification of VST from the collected supernatant or filtrate can be performed by utilizing the biochemical activity of VST, for example, the activity of suppressing GRP78 expression as described in Example 1, or through HPLC analysis and such by utilizing physical properties. For example, purification of VST may be performed via the following processes.

Crudely purified VST is obtained by extracting the culture supernatant or filtrate using a non-hydrophilic organic solvent such as ethyl acetate, followed by dehydrating the extract by concentration under reduced pressure or by using a dehydrating agent. The crude material can be further purified to a pure sample via conventional methods for purification of lipid-soluble substances such as adsorption column chromatography using carriers like silica gel, or HPLC using Senshu Pak (Senshu Scientific).

However, the above-mentioned purification method is one example, and the purification methods are not limited thereto. Therefore, other means of purification ordinarily used by those skilled in the art may be used. These include adsorption column chromatography using other adsorptive carriers, gel filtration column chromatography using resins for gel filtration, and ion exchange chromatography using anion exchange or cation exchange resins. VST may be separated and purified by using any one of these means of purification, or a combining thereof.

VST purified as described above may be used as a pharmaceutical composition, or as an intermediate for producing another compound. The dosage form of the pharmaceutical composition comprising VST is not particularly limited. In fact, the dosage form can be formulated into tablets, capsules, granules, powders, syrups, injections, etc. Furthermore, auxiliary agents such as fillers, binders, disintegrators, lubricants, corrigents and flavors, solubilizers, suspending agents and coatings may be appropriately added into such formulations within a range that does not inhibit the activity of VST.

Such compositions are effective for treating cancer, Alzheimer's disease and such; however, they are preferably used as anticancer agents. The anticancer agent of this invention is preferably an anticancer agent that induces cell death of cancer cells that are under physiological stress conditions. Herein, the physiological stress conditions include undernutritive conditions and hypoxic conditions; but are not limited thereto.

The undernutritive conditions include glucose starvation condition, low mineral condition, low lipid condition and low vitamin condition; but glucose starvation condition is preferred.

Furthermore, the anticancer agent of this invention shows a direct anticancer effect on cancer cells. However, it exerts a stronger anticancer effect, for example, in combination with other chemotherapy agents, or in conjunction with radiation treatment. Moreover, the anticancer agent of the present invention is also effective against solid cancer.

A novel substance (VST) that may decrease GRP78 expression was identified from actinomyces. Furthermore, a microorganism, *Streptomyces versipellis*, that produces this novel compound was isolated and identified. VST suppressed the expression of GRP78 increase due to agents that induce endoplasmic reticulum stress. Therefore, VST itself was shown to inhibit GRP78 expression caused by a stress response. According to these results, the use of VST suppresses the stress response mechanism of cancer cells during cancer therapy, such as chemotherapy and radiation therapy, and is effective for developing pharmaceutical agents that impart high sensitivity in cancer cells towards such chemotherapeutic agents and radiation therapy.

Any patents, published patent applications, and publications cited herein are incorporated by reference.

EXAMPLE 1

Screening

Screening for natural substances that may regulate the expression of GRP78 was performed. Specifically, herbal medicines, and respective metabolites of fungus and actinomyces were prepared as test samples. A screening system was prepared as follows. A GRP78 promoter region (−132 to +7) comprising three ERSE was inserted into the KpnI-BglII site of the multicloning site of pGL3-basic vector (Promega), and a luciferase gene was linked as a reporter gene downstream of the GRP78 promoter to construct a vector. Furthermore, pgk-neo cassette (1,867 bp) (McBurney et al., Nucleic Acids Res. 19:5755-5761 (1991)) was inserted into the SalI site of the multicloning site of the above-mentioned vector as a selection marker. The vector constructed herein (hereinafter referred to as "GRP luciferase vector") was transfected into HeLa cells. The transfection into the cells was performed by the Lipofectin method using "Transfast" (Promega). Cells carrying the GRP luciferase vector (hereinafter referred to as "HeLa78C6 cells") were selected using DMEM medium containing G418 (400 µg/mL). The selected cells were cultured in DMEM medium containing 10% FCS and 400 µg/mL G418 to prepare a HeLa78C6 cell suspension ($1.5 \times 10^5$ cells/mL).

The cell suspension (100 µL) was dispensed into each well of a 96-well plate and incubated at 37° C. in 5% $CO_2$ for 6 hours. Subsequently, the test sample (corresponding to 1 µL) was added and incubation was performed at 37° C. for 30 min. Then, tunicamycin solution was also added to each well to a final concentration of 2 µg/mL. After tunicamycin addition, incubation was performed at 37° C. for 18 hours. Then, luciferase activity of the cells was measured using a luciferase measurement kit (Luciferase Assay System: Promega, cat# E1501) following the instruction attached to the kit.

Due to the endoplasmic reticulum stress induced by the addition of tunicamycin, the expression from the GRP78 promoter was induced and luciferase activity increased. However, the increase of the luciferase activity due to tunicamycin was suppressed in the group wherein the metabolite of actinomyces strain 4083-SVS6 was added.

EXAMPLE 2

Suppression of GRP78 Expression by the Culture Supernatant of Actinomyces Strain 4083-SVS6

The actinomyces strain 4083-SVS6 shown to suppress GRP78 expression in Example 1 was precultured. A medium for the preculture (10 g starch, 10 g polypeptone, 10 g molasses and 10 g meat extract in 1 L, adjusted to pH2) was prepared and sterilized. The sterilized media (15 mL) was dispensed into a 50-mL test tube, and aseptically inoculated with actinomyces. After inoculation, culture was performed by shaking the test tube (200 rpm) at 27° C. for 3 days.

Next, main culture was performed. Specifically, a medium for the main culture (25 g starch, 15 g soybean meal, 2 g dry yeast and 4 g $CaCO_3$ in 1 L, at pH7) was prepared. The medium for the main culture (100 mL) was dispensed into a 500-mL Erlenmeyer flask with dents and the preculture solution (2 mL) was aseptically added thereto. After the addition, culture was performed with shaking (200 rpm) at 27° C. for 5 days.

The main culture was separated into culture supernatant and mycelial cake by centrifugation. Similar to Example 1, the activities to suppress GRP78 expression were measured by the reporter analysis method for the culture supernatant and mycelial cake product that was obtained by homogenizing the mycelial cake, respectively. The cell suspension solution (100 µL) was dispensed into each well of a 96-well plate and incubated at 37° C. in 5% $CO_2$ for 6 hours. Subsequently, a solution (10 µL) containing the culture supernatant (1 µL) or the mycelial cake product (1 µL) was added thereto and incubated at 37° C. for 30 min. Then, tunicamycin solution was also added to a final concentration of 2 µg/mL. After tunicamycin addition, incubation was performed at 37° C. for 18 hours. Then, luciferase activity of the cells was measured using a luciferase measurement kit. Because of the measurement, suppression of the luciferase activity was observed in the group wherein the actinomyces culture supernatant was added.

EXAMPLE 3

Purification of Active Substances from the Actinomyces Strain 4083-SVS6 Culture Supernatant 2 L main culture of actinomyces strain 4083-SVS6 was prepared similar to that of Example 1 by scaling up the culturing method. The culture solution was centrifuged at 10,000 rpm for 10 minutes, and the culture supernatant was collected to remove the mycelial cake. The collected culture supernatant was extracted with ethyl acetate and then dehydrated using sodium sulfate. The weight of the crude product after the dehydration was 2.57 g.

The dehydrated ethyl acetate extract was concentrated to dryness, then dissolved in chloroform:methanol (20:1) solution, and the solution was loaded onto a silica gel column (column capacity: 3.5φ×30 cm) to perform chromatography using the same solvent. Measurements were made on eluted samples by the reporter analysis method described in Example 1, and the eluted fractions having activity were separated (250 mg). Next, the fractions having the above-mentioned activity were collected, concentrated to dryness, dissolved in methanol, and then loaded on an HPLC column (Senshu Pak: PEGASIL ODS C18, 20 φ×250 mm; Senshu Scientific) for chromatography using 80% MeOH at a flow rate of 1 mL/min. The eluate was monitored using UV-visible light (254 nm), and the peak at a retention time 28 min was collected. The collected eluate was dried to obtain 35.7 mg of pure VST.

Figure 2:
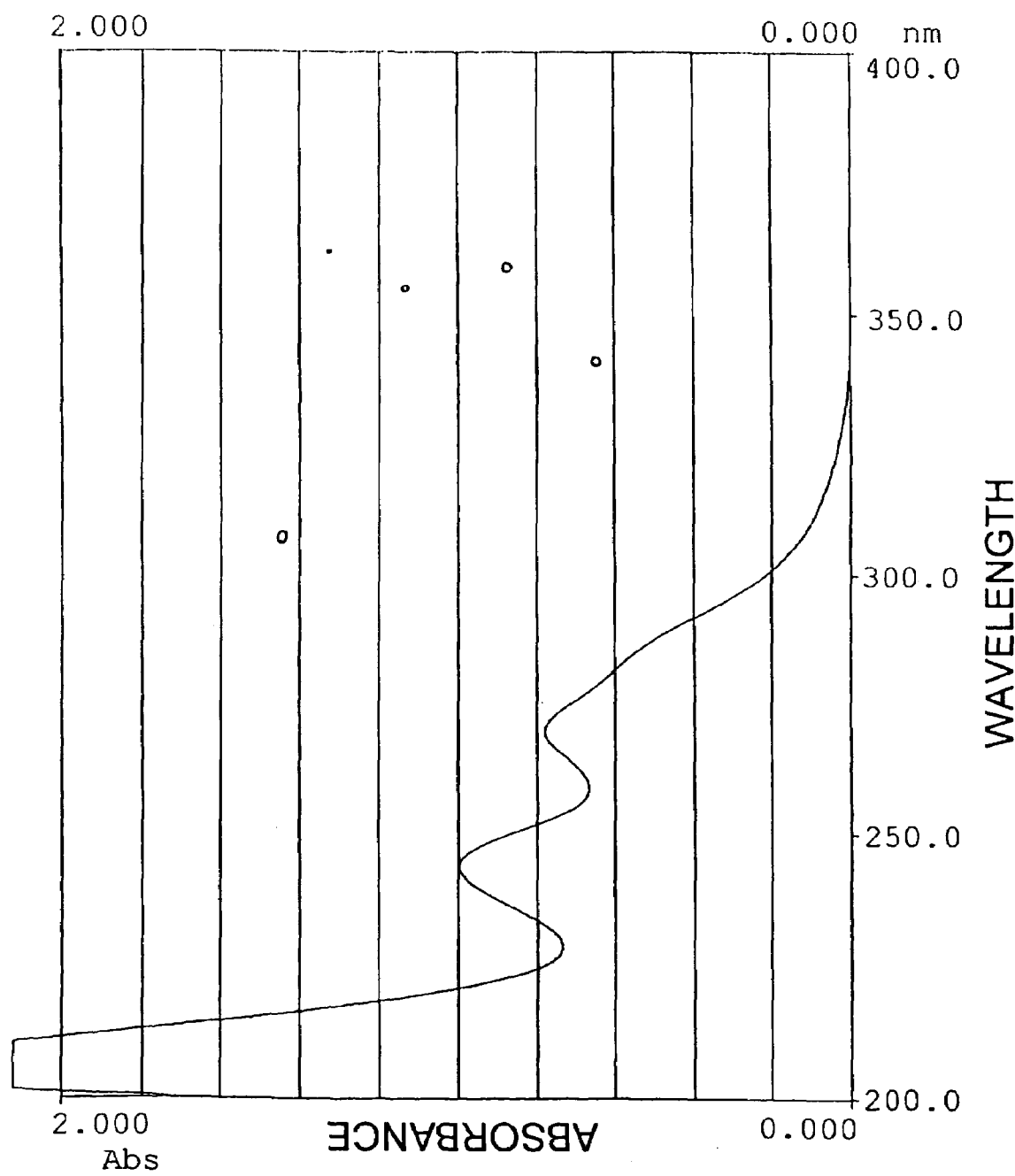
FIG. 2 shows the ultraviolet absorption spectrum of VST measured in methanol-NaOH.
Figure 3:
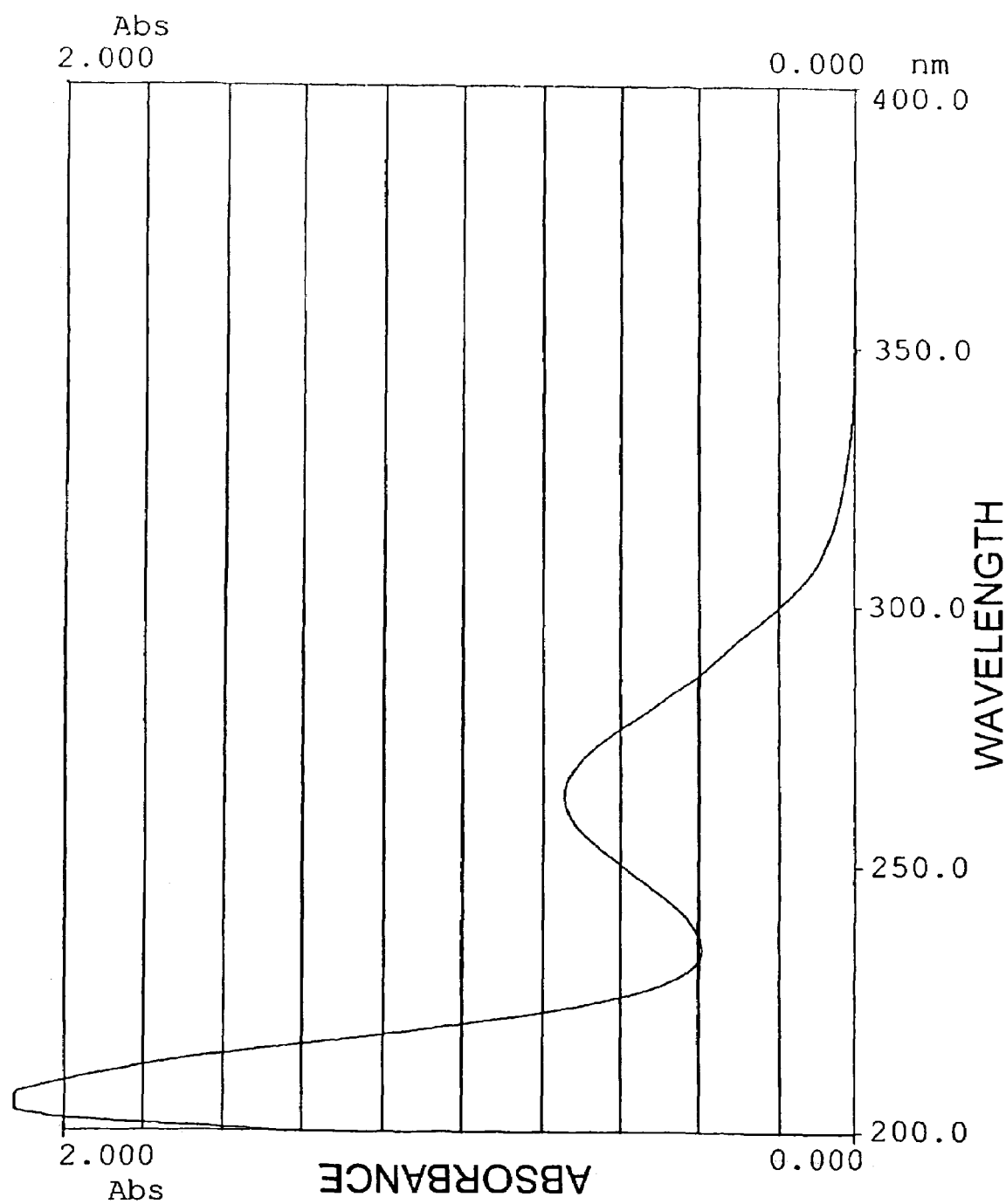
FIG. 3 shows the ultraviolet absorption spectrum of VST measured in methanol-HCl.
Figure 4:
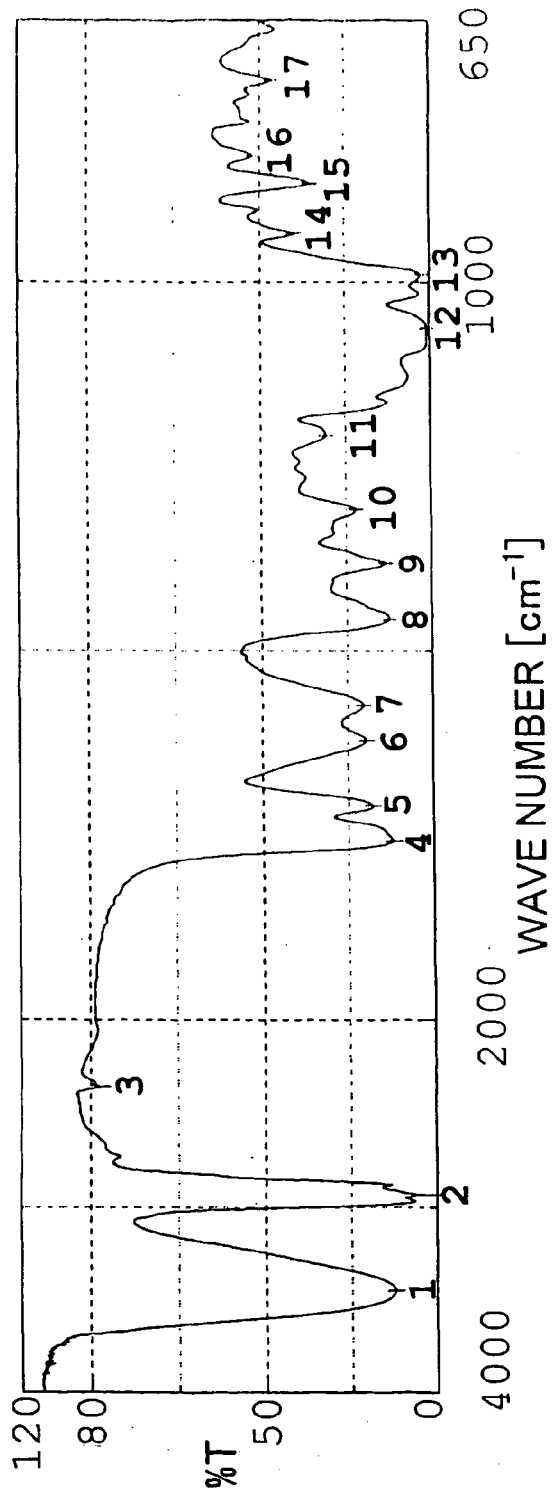
FIG. 4 shows the infrared absorption spectrum of VST measured by the potassium bromide disk method.
Figure 5:
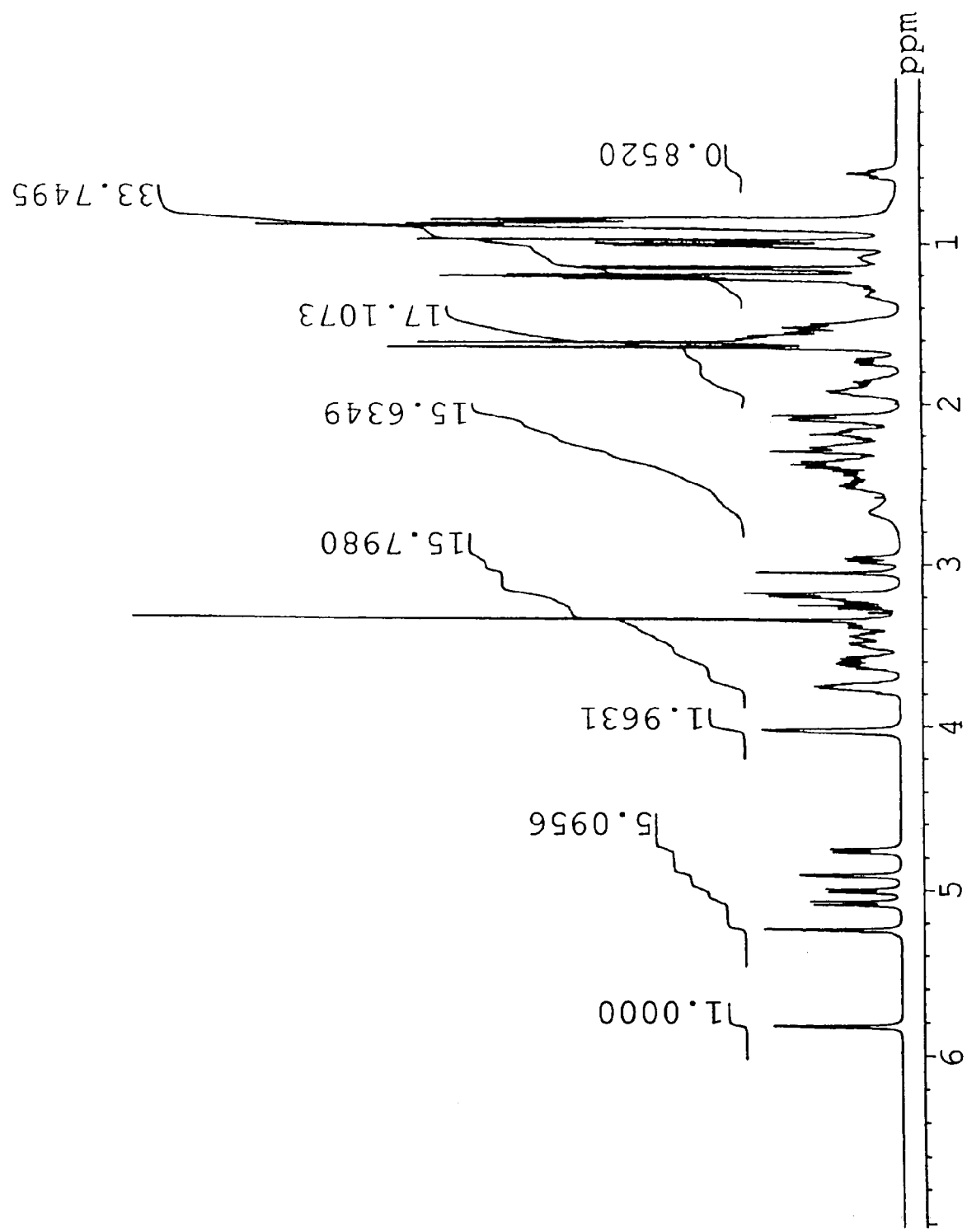
FIG. 5 shows the $^1$H-nuclear magnetic resonance spectrum of VST.
Figure 6:
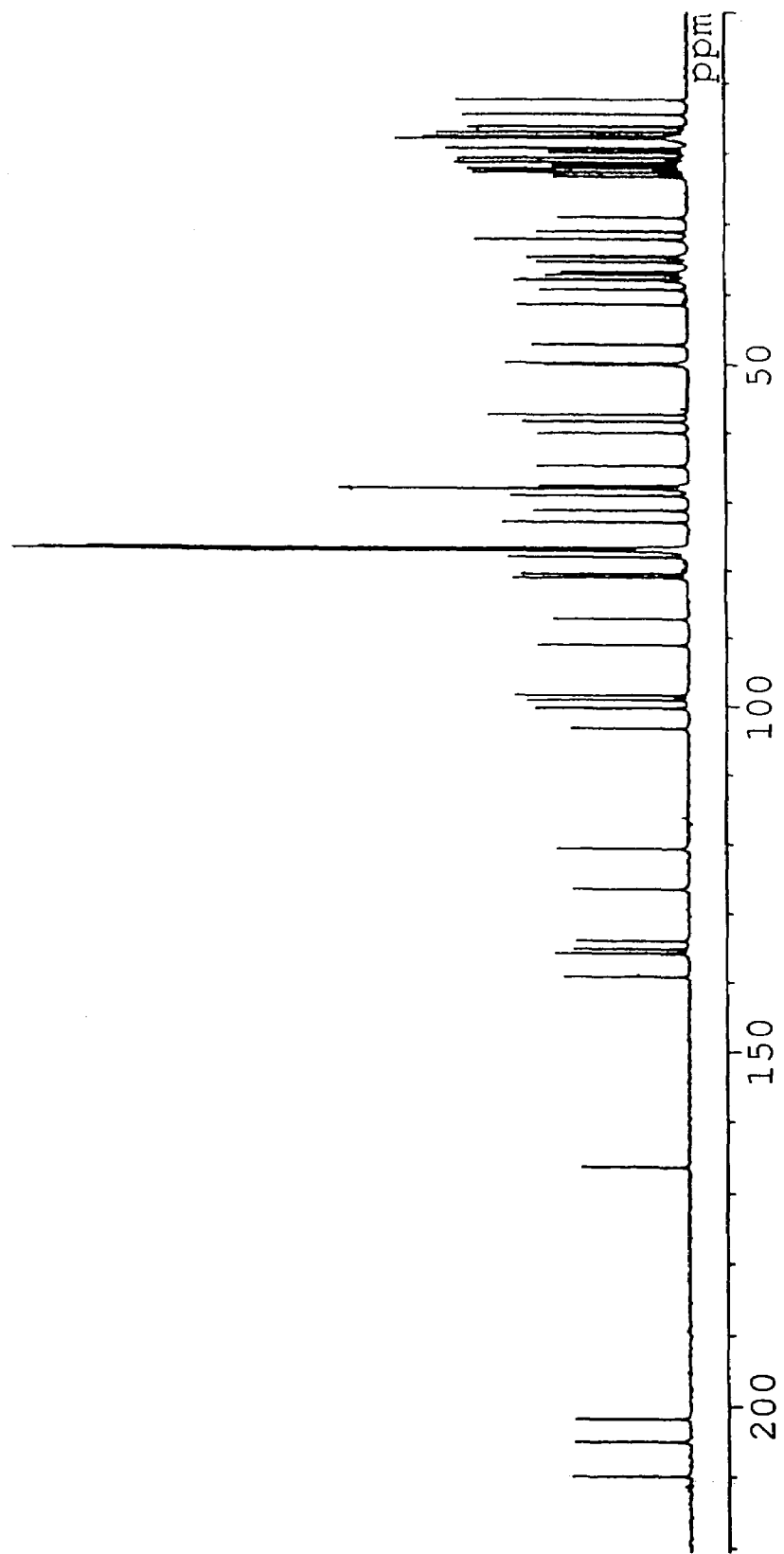
FIG. 6 shows the $^{13}$C-nuclear magnetic resonance spectrum of VST.

The physicochemical characteristics of VST are indicated below.
(1) Property of the substance: white powder.
(2) Melting point: 172-175° C.
(3) Molecular formula: $C_{61}H_9O_{17}$; (3) Molecular weight measured by FAB mass spectrometry: 1098 (M)$^-$, 1121 (M+Na)$^+$
(4) Formula (I):

(5) Precise mass measured by high-resolution FAB mass spectrometry (m/z): measured value, 1121.6398 [M+Na]$^+$; calculated value, 1121.6389.
(6) Maximum absorbance of the ultraviolet absorption spectrum (FIG. 1) measured in methanol ($\lambda_{MeOH}$ nm ($\epsilon$)): 248 (8,000), 267 (7,700); maximum absorbance of the ultraviolet absorption spectrum (FIG. 2) measured in methanol—NaOH ($\lambda_{MeOH-NaOH}$ nm ($\epsilon$)):243 (11,400), 269 (8,900); and maximum absorbance of the ultraviolet absorption spectrum (FIG. 3) measured in methanol-HCl ($\lambda_{MeOH-HCl}$ nm ($\epsilon$)): 263 (8, 500).
(7) Optical rotation measured in methanol: [α]D: −52° (c 0.8, MeOH).
(8) Maximum absorbance of the infrared absorption spectrum (FIG. 4) measured using the potassium bromide disk method (IR (KBr) λmax cm$^{-1}$): 3446, 2934, 1758, 1711, 1261, 1075.
(9) $^1$H-nuclear magnetic resonance spectrum (FIG. 5) and $^{13}$C-nuclear magnetic resonance spectrum (FIG. 6) measured at 25° C. in heavy chloroform:heavy methanol=1:1 solvent: shown in Table 4.

TABLE 4

| No. | $\delta_C$ | $\delta_H$ |
| --- | --- | --- |
| 1 | 166.35 | |
| 2 | 103.22 | |
| 3 | 205.1 | |
| 4 | 58.58 | |
| 5 | 23.44 | 2.4 |
| 6 | 49.79 | 2.46 |
| 7 | 210 | |
| 8 | 50.09 | 2.98, 2.40 |
| 9 | 71.28 | 3.78 |
| 10 | 47.18 | 2.29 |
| 11 | 120.75 | 5.84 |
| 12 | 134.16 | |
| 13 | 60.01 | 3.07 |
| 14 | 139.27 | |
| 15 | 135.94 | 5.1 |
| 16 | 37.9 | 2.28 |
| 17 | 32.23 | 1.59, 0.59 |
| 18 | 35.4 | 1.94 |

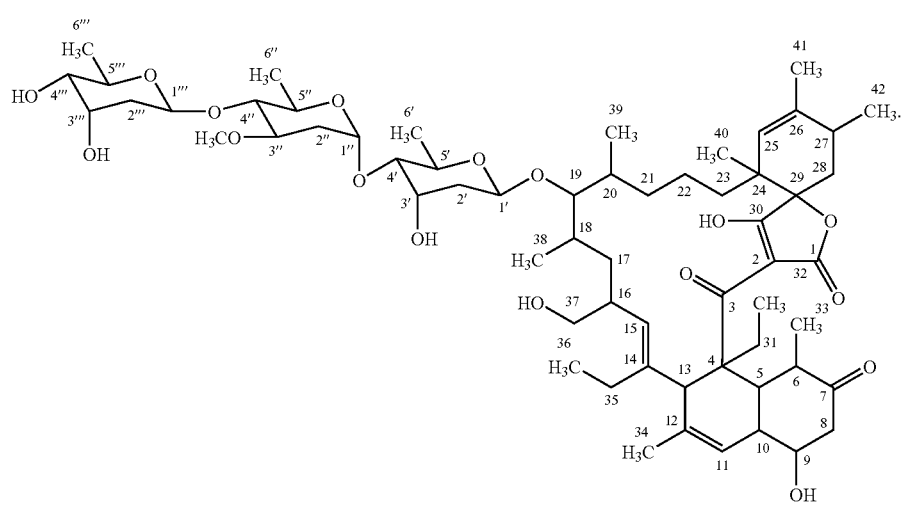

TABLE 4-continued

| No. | $\delta_C$ | $\delta_H$ |
|---|---|---|
| 19 | 91.08 | 3.2 |
| 20 | 25.19 | 1.61 |
| 21 | 32.23 | 1.49, 1.10 |
| 22 | 19.95 | 1.58, 1.33 |
| 23 | 34.56 | 1.53, 1.26 |
| 24 | 41.41 | |
| 25 | 126.63 | 5.26 |
| 26 | 135.31 | |
| 27 | 31.13 | 2.37 |
| 28 | 36.85 | 2.21, 1.75 |
| 29 | 87.31 | |
| 30 | 201.81 | |
| 31 | 23.44 | 2.52, 2.12 |
| 32 | 12.39 | 0.913 |
| 33 | 16.26 | 0.92 |
| 34 | 22.8 | 1.63 |
| 35 | 21.84 | 1.92, 1.88 |
| 36 | 14.56 | 0.88 |
| 37 | 64.72 | 3.51, 3.40 |
| 38 | 17.07 | 0.91 |
| 39 | 22.25 | 0.885 |
| 40 | 20.79 | |
| 41 | 21.41 | 1.67 |
| 42 | 19.37 | 1.03 |
| 1' | 100.3 | 4.77 |
| 2' | 37.26 | 2.11, 1.65 |
| 3' | 67.6 | 4.638 |
| 4' | 80.54 | 3.21 |
| 5' | 68.09 | 3.76 |
| 6' | 17.69 | 1.17 |
| 1" | 99.3 | 4.92 |
| 2" | 34.71 | 2.19, 1.53 |
| 3" | 73.09 | 3.46 |
| 4" | 81.13 | 3.27 |
| 5" | 68.1 | 3.6 |
| 6" | 17.97 | 1.24 |
| 3"-OCH3 | 57.25 | 3.36 |
| 1''' | 98.35 | 5.02 |
| 2''' | 38.06 | 2.10, 1.61 |
| 3''' | 68.18 | 4.044 |
| 4''' | 72.97 | 3.22 |
| 5''' | 69.15 | 3.64 |
| 6''' | 18.03 | 1.22 |

(10) HPLC analysis: column: Senshu Pak (PEGASIL ODS C18, 4.6 φ×250 mm; Senshu Scientific); solvent: 80% methanol; flow rate: 1 mL/min; detection: 254 nm; retention time: 14 min.

EXAMPLE 4

Quantitating VST Activity

Figure 7:
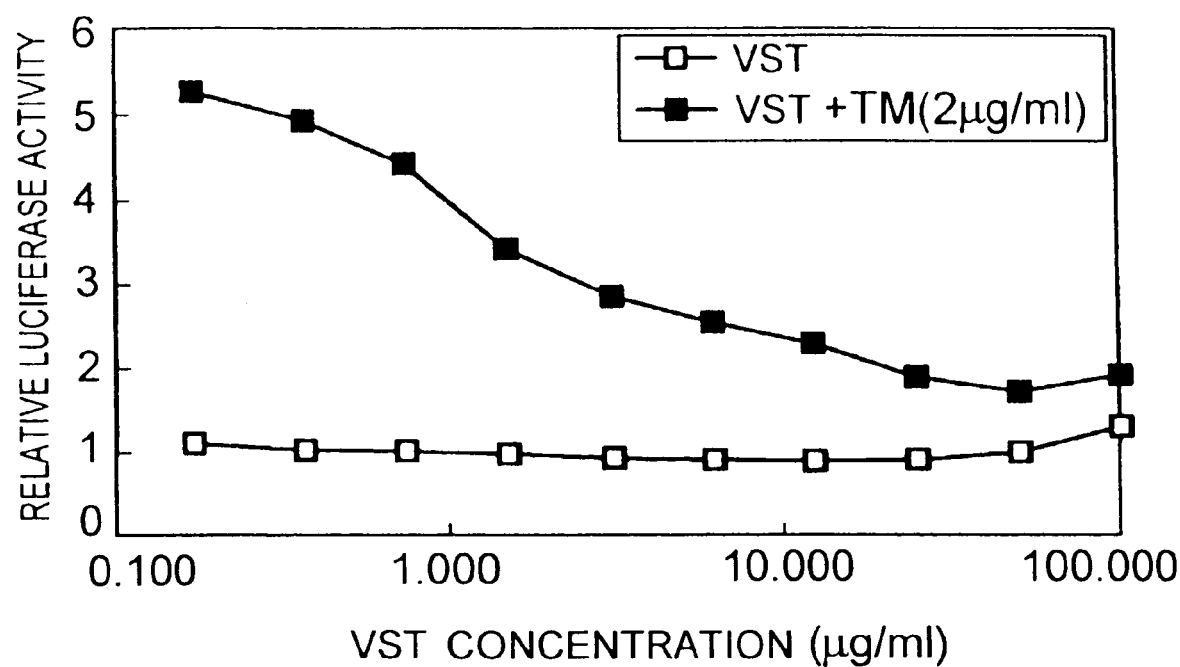
FIG. 7 shows the result of measuring the activity of VST to suppress GRP78 expression. In the figure, the solid symbols indicate the group wherein various concentrations of VST were added, and then GRP78 expression was induced by inducing endoplasmic reticulum stress in the cells via the addition of tunicamycin. The open symbols indicate the group without tunicamycin addition and wherein various concentrations of VST alone were added.

Using pure VST purified in Example 3, its activity to suppress GRP78 promoter expression was quantitated. This quantitation was also performed by the reporter analysis similar to Example 1 using the luciferase gene. Specifically, HeLa78C6 cells ($5 \times 10^5$ cells/mL, 100 μL) were dispensed into a 96-well plate as in Example 1. VST solutions diluted stepwise with methanol (100, 50, 25, 12.5, 6.25, 3.125, 1.5625 μg/mL) were prepared, and these solutions were further diluted to 10% using PBS (−). These PBS-diluted solutions (10 μL) were added to the wells (100 μL cell suspension/well). After the addition, incubation was performed at 37° C. in 5% $CO_2$ for 30 min. Subsequently, an aliquot of tunicamysin solution was also added to a part of the wells to a final concentration of 2 μg/mL. After tunicamycin addition, incubation was performed at 37° C. for 18 hours, and luciferase activity of the ultimate cells was measured using a luciferase measurement kit (Promega) (FIG. 7). The horizontal axis of FIG. 7 shows the final concentration of VST.

VST alone did not affect the expression of luciferase from the GRP78 promoter and showed the same extent of luciferase activity as the relative luciferase activity "1" that was detected in cells without sample addition. However, the luciferase expression from GRP78 increased in response to endoplasmic reticulum stress due to the addition of tunicamycin. However, the increased expression due to tunicamycin addition was suppressed in concordance with the increase in VST concentration. This result shows that VST suppresses the expression from GRP78 increased in response to the endoplasmic reticulum stress due to tunicamycin.

EXAMPLE 5

Measurement on VST Activity in Various Cells

In this Example, HeLa cells and various other culture cells were used to measure the survival rate during the above-mentioned reporter analysis and VST addition. Specifically, in addition to HeLa cells (human cervical cancer cells), MCF-7 (human breast cancer cells), PC12NH (rat pheochromocytoma), MDA-MB-231 (human breast cancer cells), TIG-3 (human normal fibroblast cells), HeLa 786C cells (human cervical cancer cells), Saos-2 (telomerase and p53-deficient human cancer cells) and SUSM-1 (telomerase-deficient human cancer cells) were used.

Figure 8:
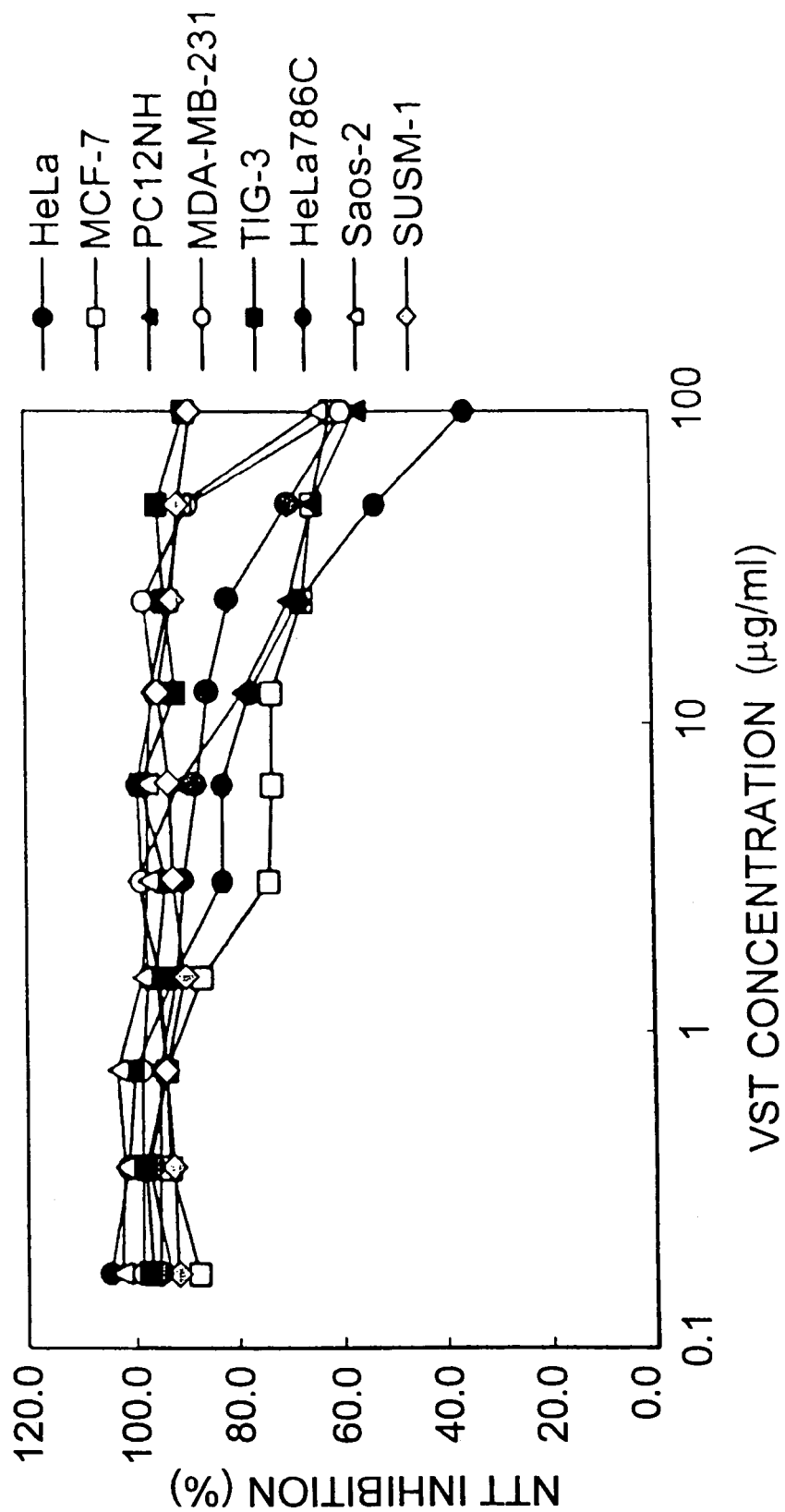
FIG. 8 shows the result of measuring direct cytotoxicity of VST based on the survival rate of a variety of cells by adding various concentrations of VST. Each symbol corresponds to respective cells indicated on the right.

The direct growth suppression activity of VST on these cells was measured using the MTT method. 100 μL cell suspension ($5 \times 10^4$/mL) of each of the above-mentioned cells was dispensed into each well of a 96-well plate and cultured for 6 hours at 37° C. After culturing, VST solution diluted stepwise as in Example 4 was added thereto and cultured for another 24 hours. After culturing for 24 hours, 0.05 g/mL MTT solution (10 μL) was added to each well and incubation was performed at 37° C. for 4 hours. The medium was then removed, DMSO (100 μL) was added, and the absorbance at 530 nm was measured (FIG. 8). The IC50s determined from these measured values are shown in Table 5.

No decrease in the survival rate was observed with VST final concentration of 1 μg/mL, and a slight decrease was observed in a few cell lines at a high concentration of approximately 10 μg/mL. By employing a higher concentration of 100 μg/mL, the survival rate of many cell lines decreased. However, the degree of decrease was kept approximately 50% at most. Furthermore, in some cell lines, no change in the survival rate could be observed even at the high concentration of 100 μg/mL. These results show that VST has low cytotoxicity, and particularly at a concentration of 1 μg/mL or less, does not exhibit direct cytotoxicity to any of the cells.

TABLE 5

| $IC_{50}$ of VST | |
|---|---|
| HeLa: | >100 μM |
| MCF-7: | >100 μM |
| PC12NH: | >100 μM |
| MDA-MB-231: | >100 μM |
| TIG-3: | >100 μM |
| HeLa786C: | 52.9 μM |
| Saos-2: | >100 μM |
| SUSM-1: | >100 μM |

EXAMPLE 6

Biological Activity of VST on HeLa78C6 Cell Line

HeLa78C6 cells were cultured in DMEM media, 30 min before tunicamycin addition each concentration of VST was added, followed by 2 µg/mL of tunicamycin, and treated for 18 hours. The cells were collected, and the induction of GRP78 was detected by Western blotting using anti-GRP78 antibody (Stressgene). As a result, it was confirmed that VST inhibits not only the reporter assay, but also the induction of endogenous molecular chaperone GRP78 at the protein level in a concentration-dependent manner (FIG. 9A).

Furthermore, HeLa78C6 was cultured by the above-mentioned culturing method and pretreated for 30 min with 50 µM VST. Then, the cells were collected at each time point after the addition of tunicamycin to detect the GRP78 protein level by Western blotting. The result revealed that GRP78 is induced 12 to 18 hours after the treatment with 2 µg/mL tunicamycin, and that this induction is inhibited by VST (FIG. 9B).

Figure 9:
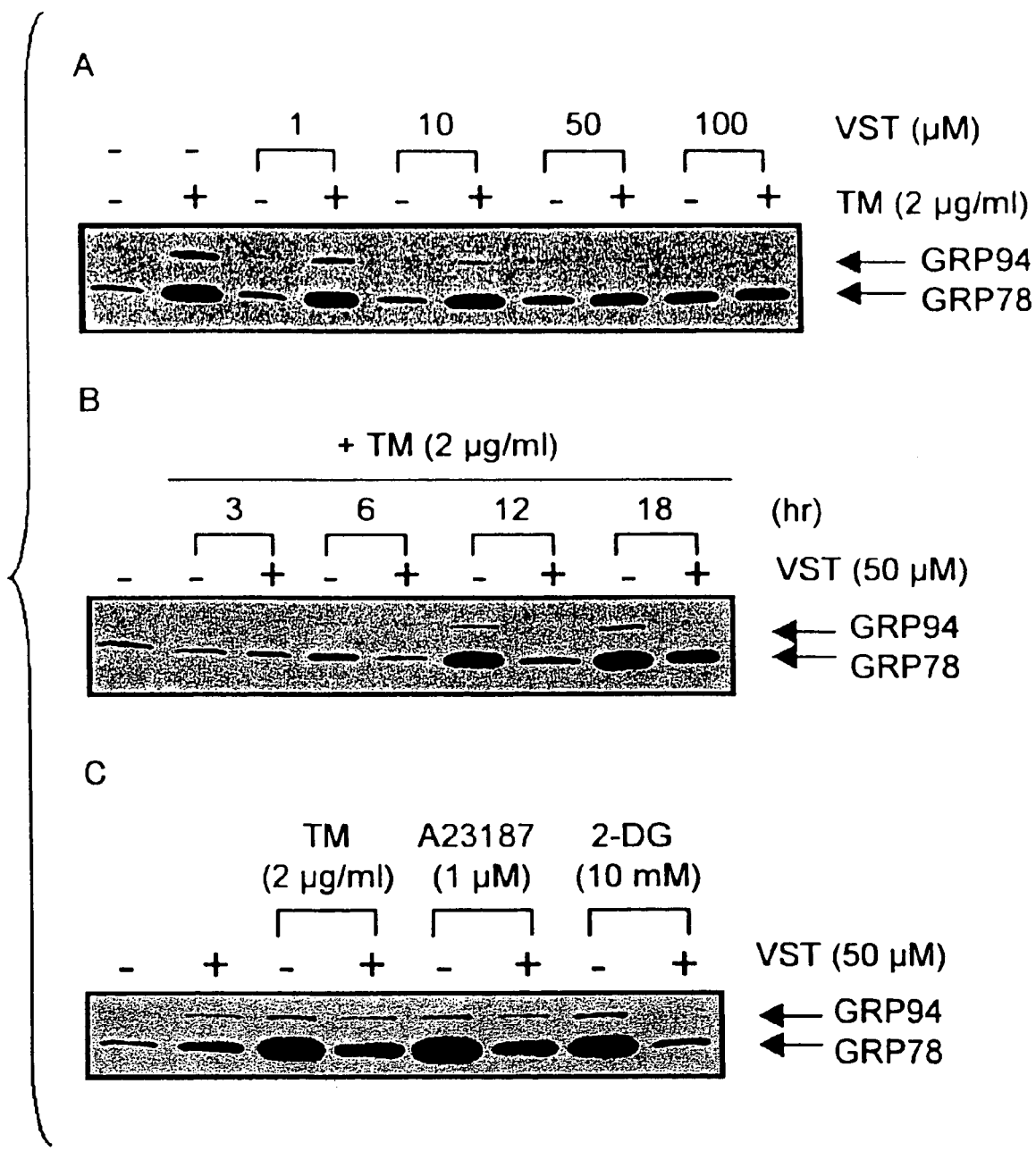
FIG. 9 is a photograph showing the activity of VST to suppress the expression of endogenous GRP78 induced by endoplasmic reticulum stress in HeLa 78C6 cells.

Moreover, the GRP78 level 18 hours after the treatment with each of the indicated endoplasmic reticulum stress-inducing agents was detected using a method similar to that used for FIG. 9A. As a result, VST inhibited the induction of GRP78 against any of the endoplasmic reticulum stresses. However, its effect showed a higher selectivity against 2-deoxyglucose (2-DG) which imitates physiological endoplasmic reticulum stress (FIG. 9C).

EXAMPLE 7

Effect of VST on GRP78 and GRP94 Levels in HT-29 and HT1080 Cells Under Various Stress Conditions Because of Example 6, VST was found to inhibit the induction of endogenous molecular chaperone GRP78 due to endoplasmic reticulum stress. Therefore, in the next step, the inhibition of GRP78 induction, apoptosis induction and effects of the combined use of other antitumor agents were examined using cancer cells, HT-29 cells and HT1080 cells that show enhanced response to endoplasmic reticulum stress among the cancer cells.

Figure 10:
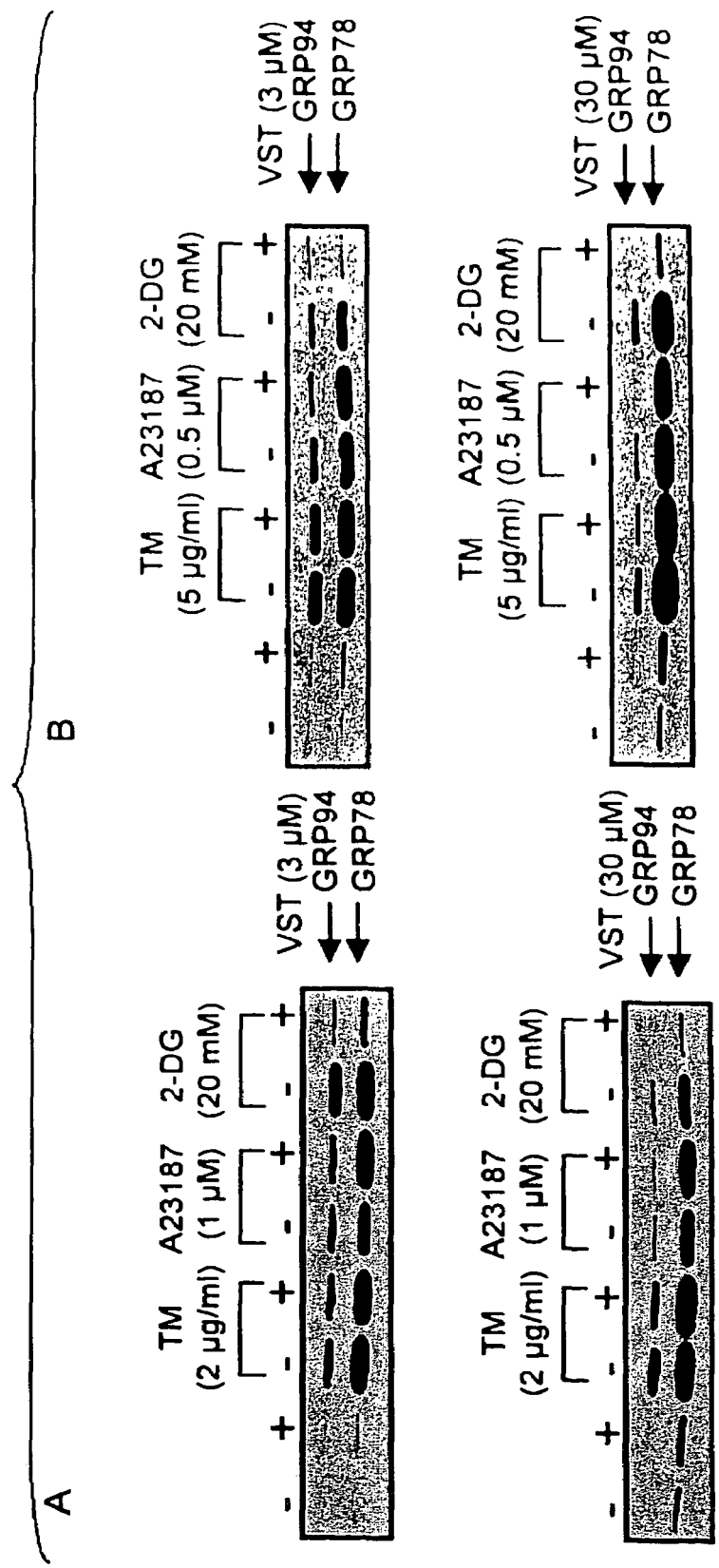
FIG. 10 is a photograph showing whether VST inhibits GRP78 expression induced by various endoplasmic reticulum stresses in endoplasmic reticulum stress hyperresponsive cancer cells, HT-29 and HT 1080.

Specifically, liver cancer cells HT-29 and HT1080 were cultured in RPMI1640 medium and pretreated for 30 min with 3 µM and 30 µM VST. Next, the GRP78 level was detected 18 hours after each endoplasmic reticulum stress treatment by Western blotting (FIG. 10). The result showed that even at a low concentration of 3 µM, VST inhibits the induction of GRP78 by 2-DG, which is a physiological endoplasmic reticulum stress in HT-29 and HT1080 cancer cells whose response to endoplasmic reticulum stress is enhanced. In contrast, even at a concentration of 30 µM, VST did not inhibit GRP78 induction due to tunicamycin treatment, which is a chemical endoplasmic reticulum stress. Furthermore, although no data is shown, VST was confirmed to exert no influence on the transcriptional activity of HSP70 heat shock protein and was demonstrated to specifically act on endoplasmic reticulum stress response. According to the present results, VST showed a particularly highly specific suppressing effect on the endoplasmic reticulum stress response in a glucose starvation experiment, a test which is a model reflecting the condition of an actual solid tumor in vivo. This suggests that the resistance mechanism can be overcome in solid cancer that is refractory to antitumor agents. Furthermore, VST was shown to be ineffective against all kinds of endoplasmic reticulum stress. This shows that the pathway of endoplasmic reticulum stress response is not exhibited through a single mechanism. This phenomenon could be elucidated for the first time by the use of VST.

EXAMPLE 8

Induction of Apoptosis Under Stress Conditions

As indicated above, VST was shown to specifically inhibit the expression of GRP78 due to glucose starvation, which is a physiological endoplasmic reticulum stress. Thus, it was further examined whether this inhibition of GRP78 induction induces cell growth suppression or apoptosis of cancer cells.

Figure 11:
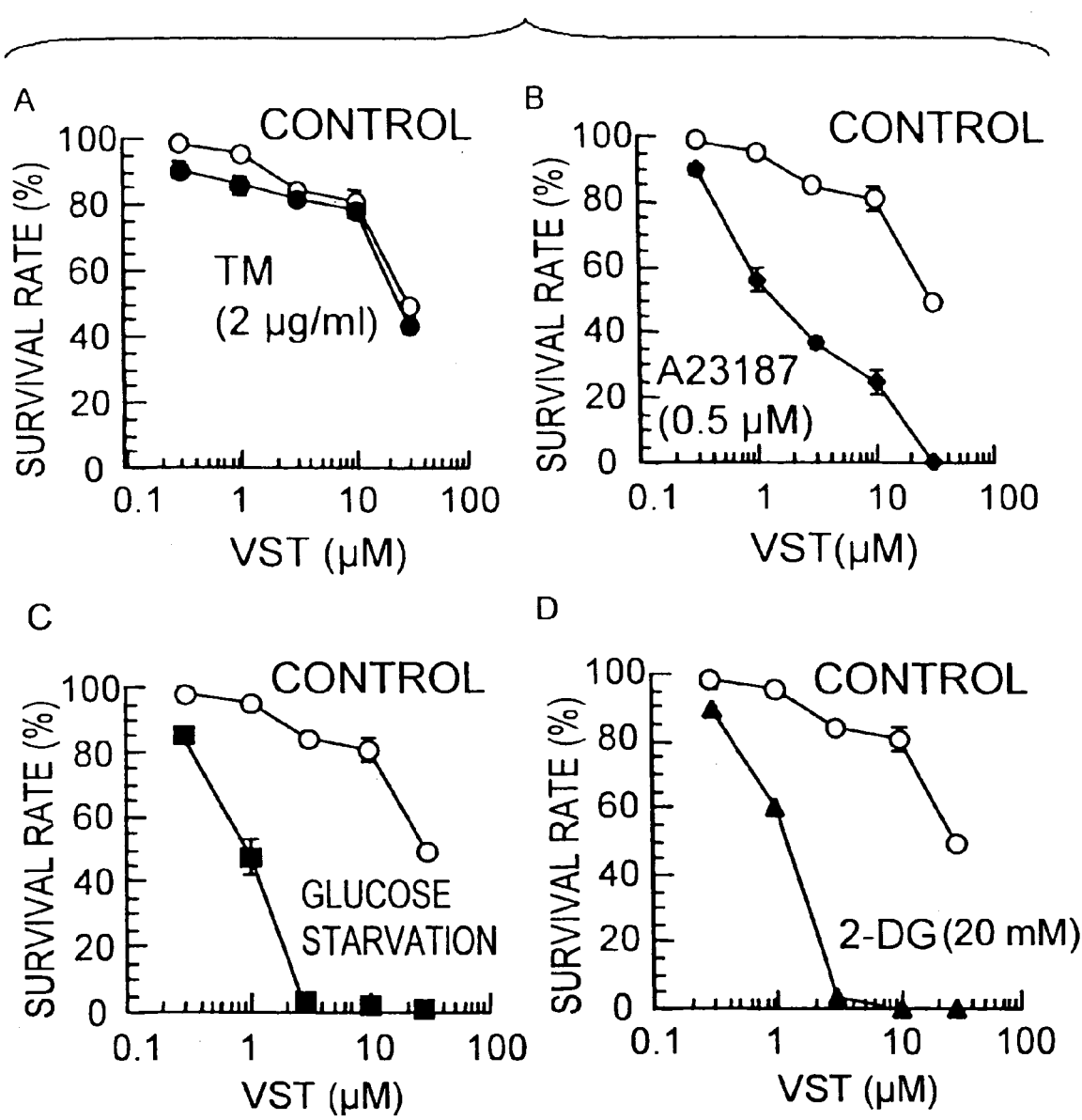
FIG. 11A shows the colony formation-inhibiting activity of VST on HT-29 cells under endoplasmic reticulum stress conditions, wherein the HT-29 cells were pretreated with VST and then subjected to stress treatment with tunicamycin.
FIG. 11B shows the colony formation-inhibiting activity of VST on HT-29 cells under endoplasmic reticulum stress conditions, wherein the HT-29 cells were pretreated with VST and then subjected to stress treatment with calcium ionophore A23187.
FIG. 11C shows the colony formation-inhibiting activity of VST on HT-29 cells under endoplasmic reticulum stress conditions, wherein the HT-29 cells were pretreated with VST and then subjected to stress treatment by glucose starvation.
FIG. 11D shows the colony formation-inhibiting activity of VST on HT-29 cells under endoplasmic reticulum stress conditions, wherein the HT-29 cells were pretreated with VST and then subjected to stress treatment with 2-DG.

HT-29 cells were pretreated for 30 min with each concentration of VST, and then subjected to stress treatment with each of the endoplasmic reticulum stresses, i.e., tunicamycin, calcium ionophore A23187, glucose starvation and 2-DG, for 18 hours. Subsequently, the cells were cultured for 1 week on a plate fixed with formalin, and then colonies were measured by crystal violet staining. As a result, VST showed a strong cell growth suppression effect proportional to the inhibition activity on GRP78 induction under glucose starvation and 2-DG treatment (FIGS. 11C and D). In contrast, under tunicamycin treatment VST did not show suppression on cell growth, a result similar to the inhibition of GRP78 induction (FIGS. 11A and B).

Figure 12:
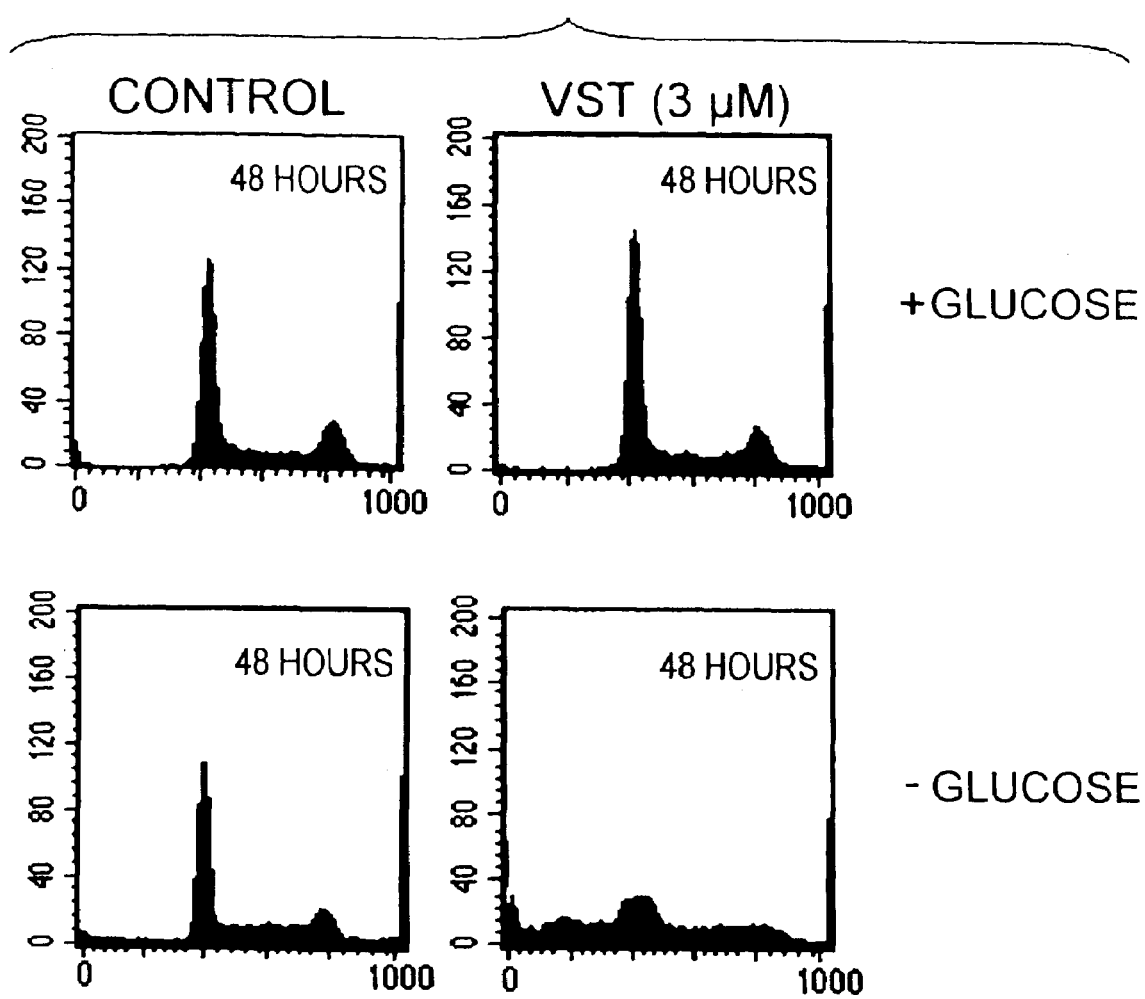
FIG. 12 shows the induction of apoptosis by VST on HT1080 cells under glucose starvation condition.
Figure 13:
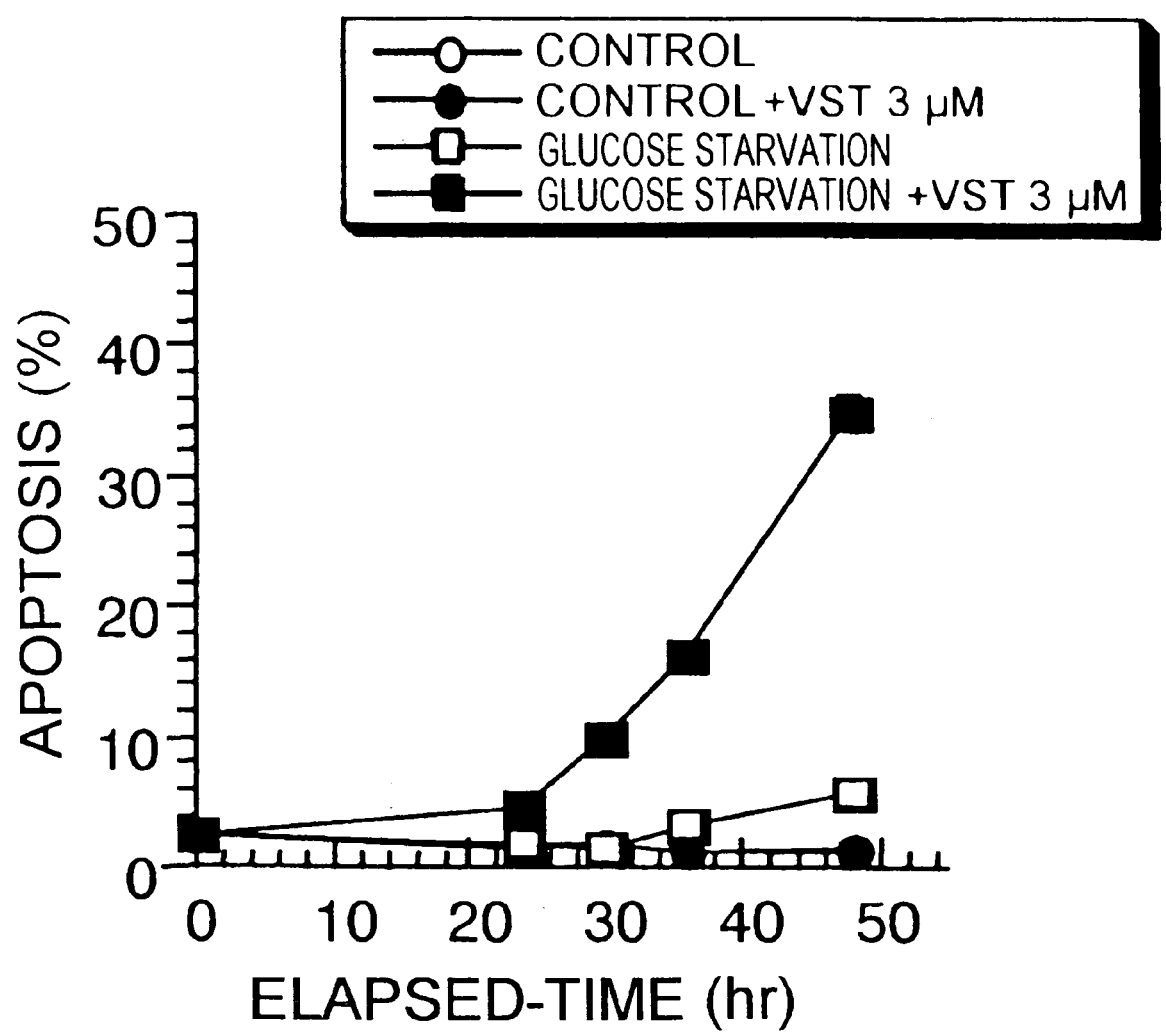
FIG. 13 shows the sequential changes upon the induction of apoptosis by VST on HT1080 cells under glucose starvation condition.

HT1080 cells were pretreated for 30 min with 3 µM of VST, after fixing the cells the nuclei were stained with propidium iodide for FACS analysis. As a result, as shown in FIG. 12, similar to the control, VST did not show any effect in the presence of glucose. However, under glucose starvation condition, VST showed strong sub-G1 stage induction after 48 hours. Thus, it was suggested that VST induces apoptosis of HT1080 cells under glucose starvation. In contrast, only a very limited number of HT1080 cells underwent apoptosis with glucose starvation treatment alone. Furthermore, as shown in FIG. 13, VST appeared to induce apoptosis of HT1080 cells under glucose starvation conditions in a time-dependent manner.

The above-mentioned results revealed that VST specifically induces cell death of cancer cells under glucose starvation conditions by inhibiting the induction of GRP78.

EXAMPLE 9

Activity of the Combined use of VST and Anticancer Agents

Enhancement of endoplasmic reticulum stress response promotes survival of cells under undernutritive conditions, and at the same time allows cells to acquire resistance to antitumor agents. Therefore, the inventors intended to examine the effect of VST on known antitumor agents. However, in experiments at the cellular level, even used alone, VST shows strong apoptosis induction under glucose starvation condition. Therefore, the combined effect with other pharmaceutical agents could not be duly examined. Thus, cisplatin generally used for solid cancer treatment was used to examine the combined effect, due to its activity on cancer cells that is maintained even under low glucose conditions. Specifically, HT-29 cells were cultured by the above-mentioned method, pretreated for 30 min with VST, and then cultured for 18 hours. The cells were then treated for 4 hours with each concentration of cisplatin, and a week later their colony-forming ability was examined.

Figure 14:
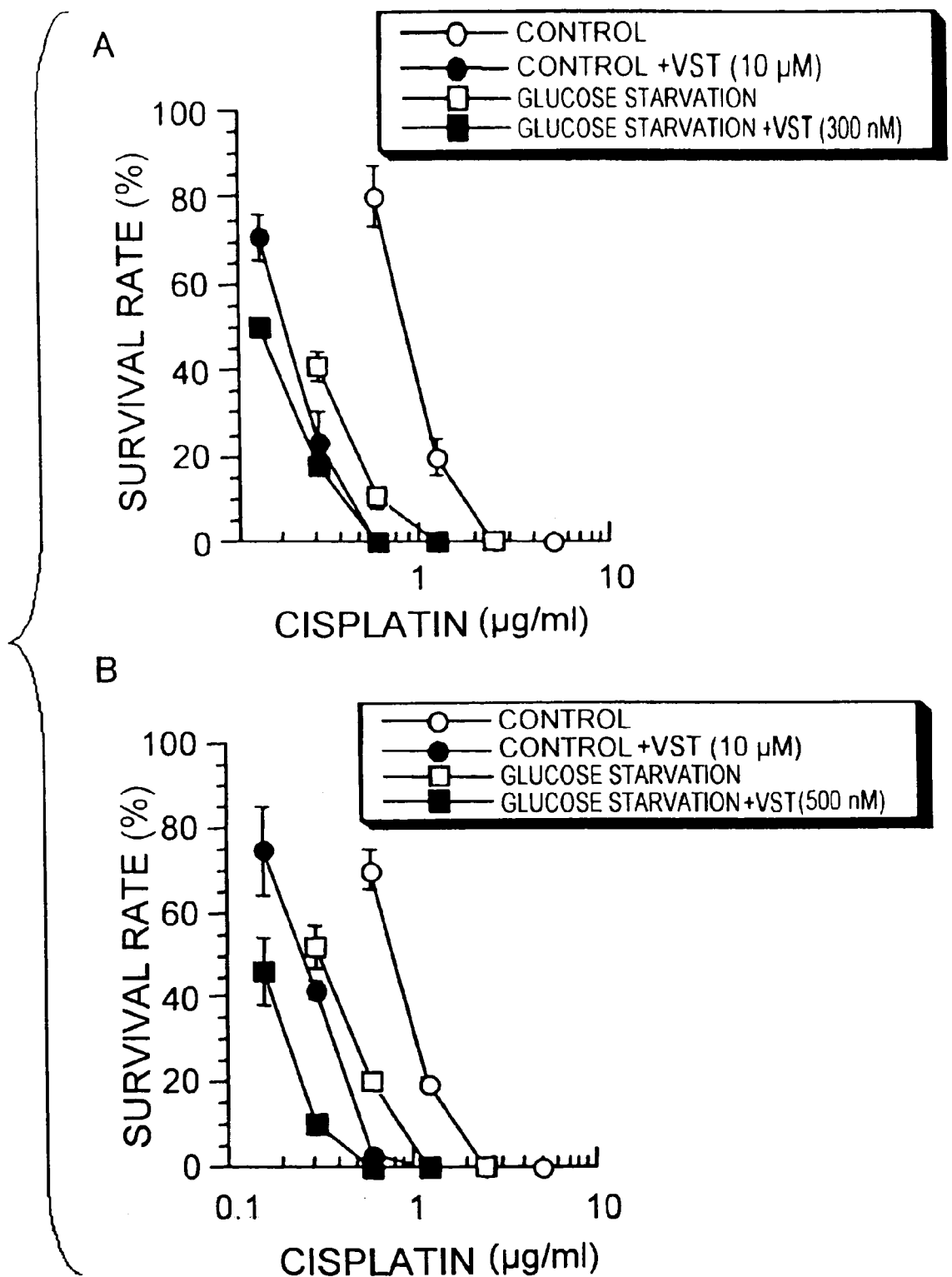
FIG. 14A shows the effect of the combined use of 300 nM VST and the antitumor agent cisplatin against solid cancer
FIG. 14B shows the effect of the combined use of 500 nM of VST and the antitumor agent cisplatin against solid cancer.

As a result, both VST and cisplatin were confirmed to enhance the activity under glucose starvation condition. Furthermore, the addition of VST at low concentrations (300 nM and 500 nM) was found to further enhance the effect of cisplatin (FIG. 14).

Cisplatin is generally used for solid cancer treatment; however, it is known to have strong side effects. Therefore, when the dose of cisplatin can be lowered by the use of VST, it may greatly contribute to the patient's quality of life (QOL).

EXAMPLE 10

Animal Testing

Figure 15:
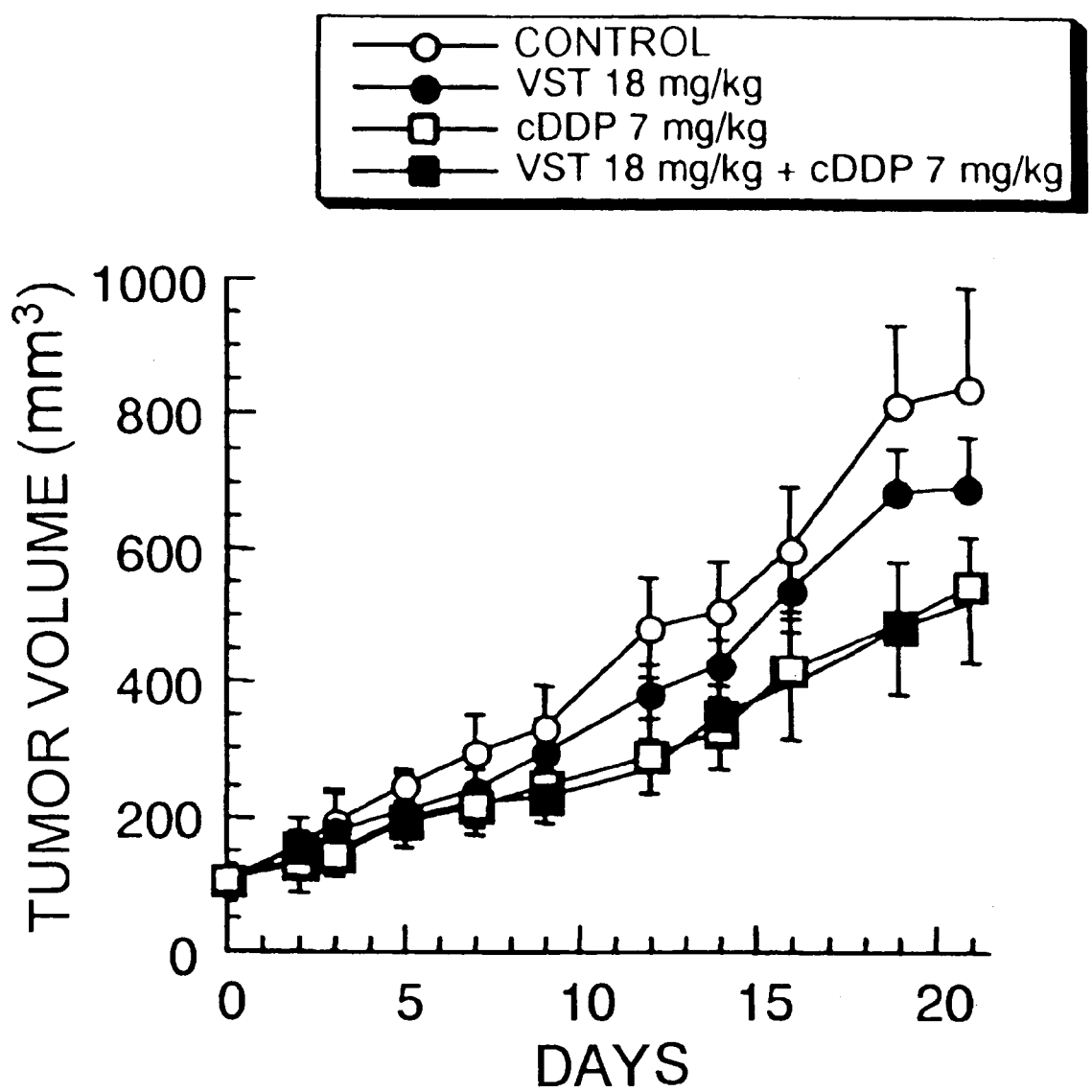
FIG. 15 shows the antitumor effect of VST at the animal level against HT-29 cancer cells in nude mice.

The antitumor effect of VST at the animal level was examined. Specifically, HT-29 cells were transplanted into nude mice and tumor was grown to 100 mm$^3$. Subsequently, each concentration of VST was administered through the tail vein, progress of cancer was followed each day thereafter, and the tumor was enucleated to compare its size. The result is shown in FIG. 15. VST showed antitumor effect, although the effect was not as strong as cisplatin. Furthermore, the combined effect with CDDP (cisplatin) was examined. However, the effect of cisplatin was sufficient and no effect due to the combination could be confirmed.

Since the in vitro strong effect could not be confirmed in the animal experiment, the apoptosis inducing effect of VST on HT-29 cells was reexamined. The result revealed that VST shows growth suppression effect in colony forming tests but fails to express apoptosis induction effect.

EXAMPLE 11

Mechanism Elucidation Studies

To elucidate the mechanism of VST to express its activity, the effect of VST on several factors that function in the pathway of endoplasmic reticulum stress response was examined. In particular, Ire1α-XBP1 pathway, a pathway of endoplasmic reticulum stress response and is widely conserved from yeast to mammalian cells, was examined. XBP1 spliced at the mRNA level from a precursor (XBP1 (U)) by Ire1α, that is activated in response to endoplasmic reticulum stress turns into the activated form (XBP1(S)), transfers to the nucleus, and induces transcription of GRP78 by binding to the GRP78 promoter, ERSE.

Figure 16:
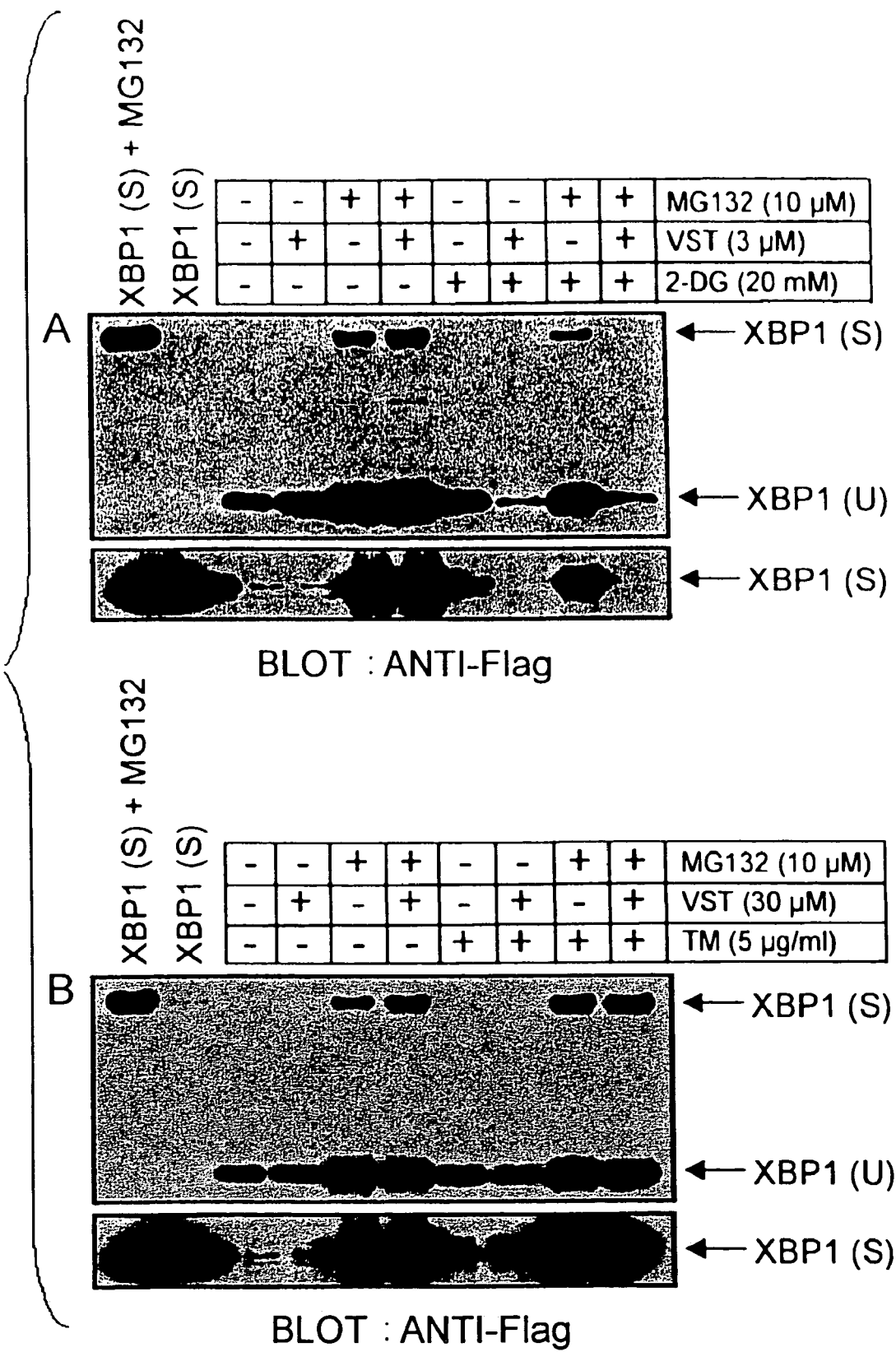
FIG. 16A shows the formation of spliced XBP-1 as a result of 2-DG treatment.
FIG. 16B shows the formation of spliced XBP-1 as a result of tunicamycin treatment.

A plasmid wherein a Flag tag is linked to the cloned XBP1 was transfected into HT1080, and the cell was pretreated for 30 min with VST. 6 hours after imposing each stress, proteasome inhibitor MG132 was added and the cells were cultured for another 6 hours to prepare samples. The full length and spliced XBP1 were detected in the samples using anti-Flag antibody. Examination on the formation of the spliced form XBP1 due to 2-DG treatment is shown in FIG. 16A and that due to tunicamycin treatment is shown in FIG. 16B. Since the spliced form of XBP1 is very rapidly degraded by proteasomes, its detection is difficult. To overcome this problem, proteasome inhibitor MG132 was added. Comparing the two lanes on the right in FIGS. 16A and B, the formation of spliced XBP1 was found to be inhibited by the addition of VST in the 2-DG treatment. In contrast, VST did not inhibit the splicing of XBP1 due to tunicamycin. This suggests that the mechanism of endoplasmic reticulum stress response differs between tunicamycin and glucose starvation at the XBP1 activation level. The novel findings obtained by the results of the present invention were discovered for the first time due to the discovery of VST. Furthermore, apart from VST, no other substance has been reported to inhibit the splicing of XBP1.

What is claimed is:

1. A purified, isolated versipelostatin compound according to the following formula (I):

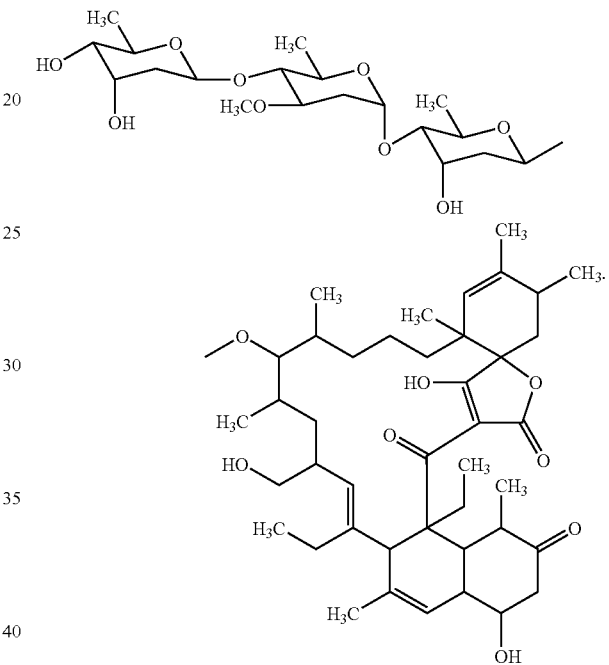

2. A method for producing the compound of claim 1, which comprises the steps of culturing *Streptomyces versipellis* strain 4083-SVS6 (FERM BP-8179) to produce the compound of claim 1, and collecting the compound from the culture.

3. A composition comprising the compound of claim 1 or a pharmaceutically acceptable salt thereof.

4. The composition of claim 3, which induces cell death in cancer cells in a cell culture that are under physiological stress condition.

5. The composition of claim 4, wherein the physiological stress condition is an undenutritive condition or a hypoxic condition.

6. The composition of claim 3, which exhibits anticancer effect against solid cancer in a test animal wherein the solid cancer is the result of implantation of cancer cells in said test animal.

* * * * *